(12) United States Patent
Chen et al.

(10) Patent No.: US 6,986,902 B1
(45) Date of Patent: Jan. 17, 2006

(54) POLYANIONIC POLYMERS WHICH ENHANCE FUSOGENICITY

(75) Inventors: Tao Chen, Richmond (CA); Yuehua He, Vancouver (CA); Peter Cullis, Vancouver (CA); Thomas Madden, Vancouver (CA); Peter Scherrer, Vancouver (CA); David Tirrell, Sunderland, MA (US); Phalgun Joshi, Vancouver (CA); Jung Soo Kim, Amherst, MA (US)

(73) Assignee: Inex Pharmaceuticals Corporation, Burnaby (CA)

( * ) Notice: Subject to any disclaimer, the term of this patent is extended or adjusted under 35 U.S.C. 154(b) by 0 days.

(21) Appl. No.: 09/674,191

(22) PCT Filed: Apr. 27, 1999
(Under 37 CFR 1.47)

(86) PCT No.: PCT/US99/09076

§ 371 (c)(1),
(2), (4) Date: May 21, 2002

(87) PCT Pub. No.: WO99/55743

PCT Pub. Date: Nov. 4, 1999

Related U.S. Application Data

(60) Provisional application No. 60/083,294, filed on Apr. 28, 1998.

(51) Int. Cl.
A61K 9/127 (2006.01)
C08G 63/48 (2006.01)
C08G 67/02 (2006.01)
C08F 265/08 (2006.01)

(52) U.S. Cl. .................. 424/450; 424/1.21; 424/9.321; 424/9.51; 525/7; 525/50; 525/295; 528/392

(58) Field of Classification Search ............... 424/450, 424/1.21, 9.321, 9.1; 428/402.2; 525/7, 525/50, 295; 528/392
See application file for complete search history.

(56) References Cited

U.S. PATENT DOCUMENTS 4,118,554 A 10/1978 Fields et al.
4,921,757 A * 5/1990 Wheatley et al. ........ 428/402.2

(Continued)

FOREIGN PATENT DOCUMENTS

EP 0 710 666 A 5/1996

(Continued)

OTHER PUBLICATIONS

E. Klesper, "H-NMR Study of the Esterification of Syndiotactic Poly(metharyclic Acid) with Carbodiimides"; *Journal of Polymer Science*, Polymer Letters Edition, vol. 15, No. 1, Jan. 1977, pp. 23-29.

*Primary Examiner*—Gollamudi S. Kishore
(74) *Attorney, Agent, or Firm*—Oppedahl & Larson LLP

(57) ABSTRACT

The present invention relates generally to the amphiphilic polyelectrolyte, poly(2-ethylacrylic acid) and covalently bonded lipids to generate Lipo-PEAA. These Lipo-PEAA are then used to make pH-sensitive liposomes which become unstable, permeable or fusogenic with certain pH changes. In addition, this invention generally describes methods for delivering therapeutic compounds and drugs to target cells by administering to a host the pH-sensitive liposomes of the present invention.

46 Claims, 14 Drawing Sheets

U.S. PATENT DOCUMENTS

| | | | |
|---|---|---|---|
| 5,013,556 A * | 5/1991 | Woodle et al. | 424/450 |
| 5,180,782 A | 1/1993 | Stone et al. | |
| 5,395,619 A * | 3/1995 | Zalipsky et al. | 424/450 |
| 5,498,420 A * | 3/1996 | Mentrup Edgar et al. | 424/450 |
| 5,500,161 A * | 3/1996 | Andrianov et al. | 264/8 |
| 5,723,599 A | 3/1998 | Klem et al. | |
| 5,935,599 A * | 8/1999 | Dadey | 424/450 |

FOREIGN PATENT DOCUMENTS

| | | |
|---|---|---|
| WO | WO 92 05778 A | 4/1992 |

* cited by examiner

Figure 13. Illustrates the intracellular calcein release and inhibition study of PEAA-lipid particle(calcein)s with terminal anchored PEAA.
Intracellular calcein release
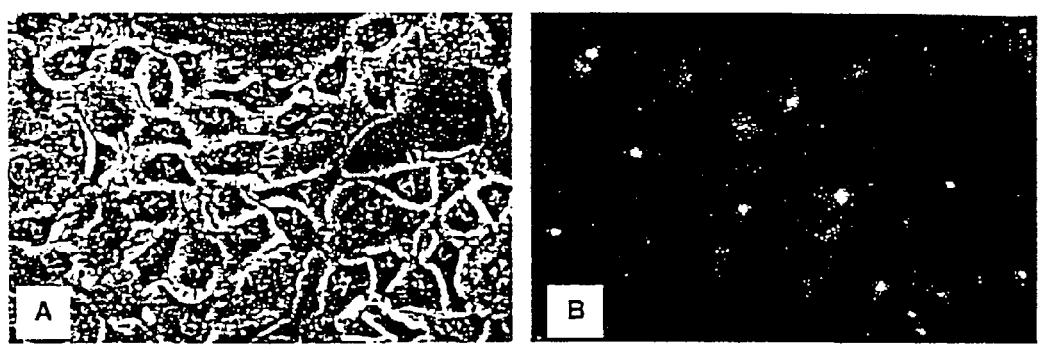
Calcein release was inhibited by chloroquine
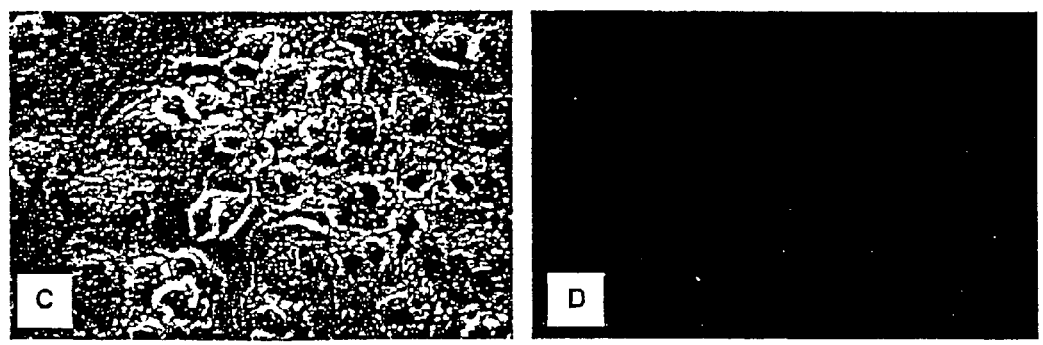
A and C for phase contrast, and B and D for fluorescence

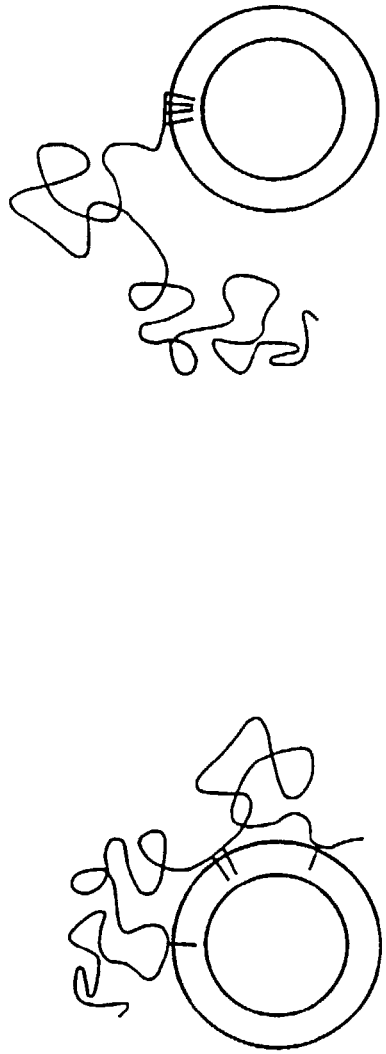
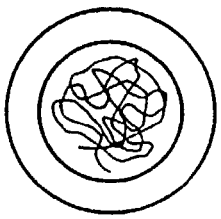
Fig. 14
A. Preparation of PEAA-LUVs by Coating Method
Random Anchored PEAA
Terminal Anchored PEAA
B. Encapsulation of PEAA Inside of LUVs

POLYANIONIC POLYMERS WHICH ENHANCE FUSOGENICITY

This application claims the benefit of Provisional Application No. 60/083,294, file Apr. 28, 1998.

BACKGROUND OF THE INVENTION

In the medical field, the generally preferred and most effective method of treatment is to target delivery of a pharmaceutical drug or agent to the diseased site without compromising the well being of the patient. In this regard, the importance of liposomes as drug delivery vehicles has now been recognized. Recently, liposomes have been widely used as drug carriers because they are able to function both as a controlled release system and as a delivery system for transporting encapsulated compounds to cells. More importantly, the innate ability of liposomes to reduce the toxicity of entrapped bioactive agents while maintaining efficacy is the reason why the use of liposomes has become popular. Some areas in which liposomes display therapeutic promise are as carriers for anticancer agents, antifungal agents, antibacterials, antivirals, and antiparasitics. More recently, the application of liposomes has been seen in the areas of gene therapy.

Within the cells, the majority of the liposomes are internalized through an endocytotic pathway and then subsequently enzymatically degraded. These delivery agents, when endocytosed, eventually end up in the acidic interior of endosomes having a pH between 5 and 6, and are ultimately converted into lysosomes. The acidic barrier defeats the use of liposomes as an intracellular delivery system.

Therefore, a target delivery system using pH-sensitive drug carriers is needed, wherein a pH-sensitive fusogenic system allows the payload of the delivery agent to escape from the endosomal compartment before the therapeutic agents are hydrolytically degraded. Liposomes that are dependent upon the pH of the environment are referred to as pH-sensitive liposomes.

Most pH-sensitive liposomal systems have utilized the strong tendency of unsaturated phosphatidylethanolamine (PE), as the phospholipid component, to form a non-bilayer structure and promote fusion (see, Ellens, et al., *Biochemistry*, 23:1532–1538 (1984)). Unsaturated PE does not form liposomes by itself, but liposomes can be prepared from unsaturated PE by incorporation of various pH-sensitive amphiphiles having a carboxyl group to stabilize the liposomal system. The stabilizing ability of these amphiphiles is designed to decrease under acidic conditions and/or cause destabilization and fusion of the liposomes.

However, this type of pH-sensitive liposome has several disadvantages. The stability of the liposomes is poor compared to phosphatidylcholine-based liposomes. For example, it has been reported that pH-sensitive liposomes composed of unsaturated PE and oleic acid (OA) rapidly aggregate and become leaky in the presence of plasma (see, Connor, et al., *Biochim. Biophys. Acta.*, 884:474–481 (1986)). An attempt was made to increase the stability of PE/OA liposomes in serum by adding cholesterol. However, this attempt proved to be unsuccessful and as a consequence the pH sensitivity of the liposome was reduced.

More recently, polyanionic polymers having titratable functional groups attached, such as poly(2-ethylacrylic acid) (PEAA) and succinylated poly(glycidol) (see, Kono, et al., *Biochim. Biophys. Acta.*, 1193:1–9 (1993)), have been reported to mediate proton-induced release of liposomal contents when the pH was reduced below the physiological pH. Moreover, the use of a phospholipid vesicle and the amphiphilic polyelectrolyte, poly(2-ethylacrylic acid) have previously been described in the art in U.S. Pat. No. 4,833,061. In addition, a pH-sensitive liposome was developed by immobilization of poly(2-ethylacrylic acid) on the surface of small unilamellar vesicles (SUVs) through the linking of polyelectrolytes bearing thiol functional groups to vesicles bearing maleimido functional groups, the SUV's being prepared by sonication of a dried egg phosphatidylcholine (EPC) film in buffered solutions (see, Maeda, et al. *J. Am. Chem. Soc.*, 110:7455–7459 (1988)). However, the use of poly(2-ethylacrylic acid) conjugated to the surface of the SUVs resulted in an inconsistency or variation in the amount of entrapped calcein released upon acidification.

What is needed in the art is a pH-sensitive liposome whose fusogenicity and/or permeability can be readily controlled by a change in the pH of its environment. Preferably, this control should be engineered into the liposome architecture. This invention fulfills this and other needs.

SUMMARY OF THE INVENTION

In one aspect, this invention relates to a compound having the following general formula:

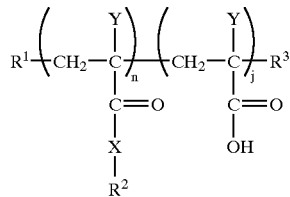

In Formula I, $R^1$ is a functional group including, but not limited to, hydrogen, hydroxyl, amino, optionally-substituted alkyl and a ligand.

In Formula I, Y is a functional group including, but not limited to hydrogen, optionally-substituted alkyl, optionally-substituted cycloalkyl, optionally-substituted aryl and optionally-substituted heteroaryl.

In Formula I, X is a functional group including, but not limited to, optionally-substituted amino, oxygen, sulfur and a carbon single bond.

In Formula I, $R^2$ is a functional group including, but not limited to, hydrogen, alkyl, alkenyl, dialkylglycerolyl, dialkenylglycerolyl, diacylglycerolyl, 1,2-diacyl-sn-glycero-3-phosphoethylenyl, 1,2-dialkoxy-3-aminopropanyl and 1,2-diacyloxy-3-aminopropanyl. In Formula I, X and $R^2$ can be combined to form an aminoalkyl group.

In Formula I, $R^3$ is a functional group including, but not limited to, hydrogen, hydroxyl, amino, optionally-substituted alkyl and a ligand.

In Formula I, the index "n" is an integer greater than 1 and the index "i" is an integer greater than 1.

In another aspect, this invention relates to a pH-sensitive liposome, a micelle, a virosome, a lipid-nucleic acid particle, or other drug delivery composition having a lipid and a compound of Formula I. In a presently preferred embodiment, the pH-sensitive liposome is fusogenic.

In yet another aspect, this invention relates to a method for delivering a therapeutic compound to a target cell, the method comprising administering to a host containing the target cell a pH-sensitive liposome which has a lipid, a compound of Formula I and the therapeutic compound.

Additional features and advantages of the present invention will become apparent from the following detailed description, taken in conjunction with the accompanying drawings which illustrate, by way of example, the principles of the invention.

BRIEF DESCRIPTION OF THE DRAWINGS

FIG. 13 illustrates the intracellular calcein release and inhibition study of PEAA-Lipid particle(calcein)s synthesized by the anionic polymerization method.

FIG. 14 illustrates the general scheme of using a lipo-PEAA, which is derivatized either through the random point method or the anionic polymerization method, with lipid particles.

DESCRIPTION OF THE SPECIFIC EMBODIMENTS

Figure 1:
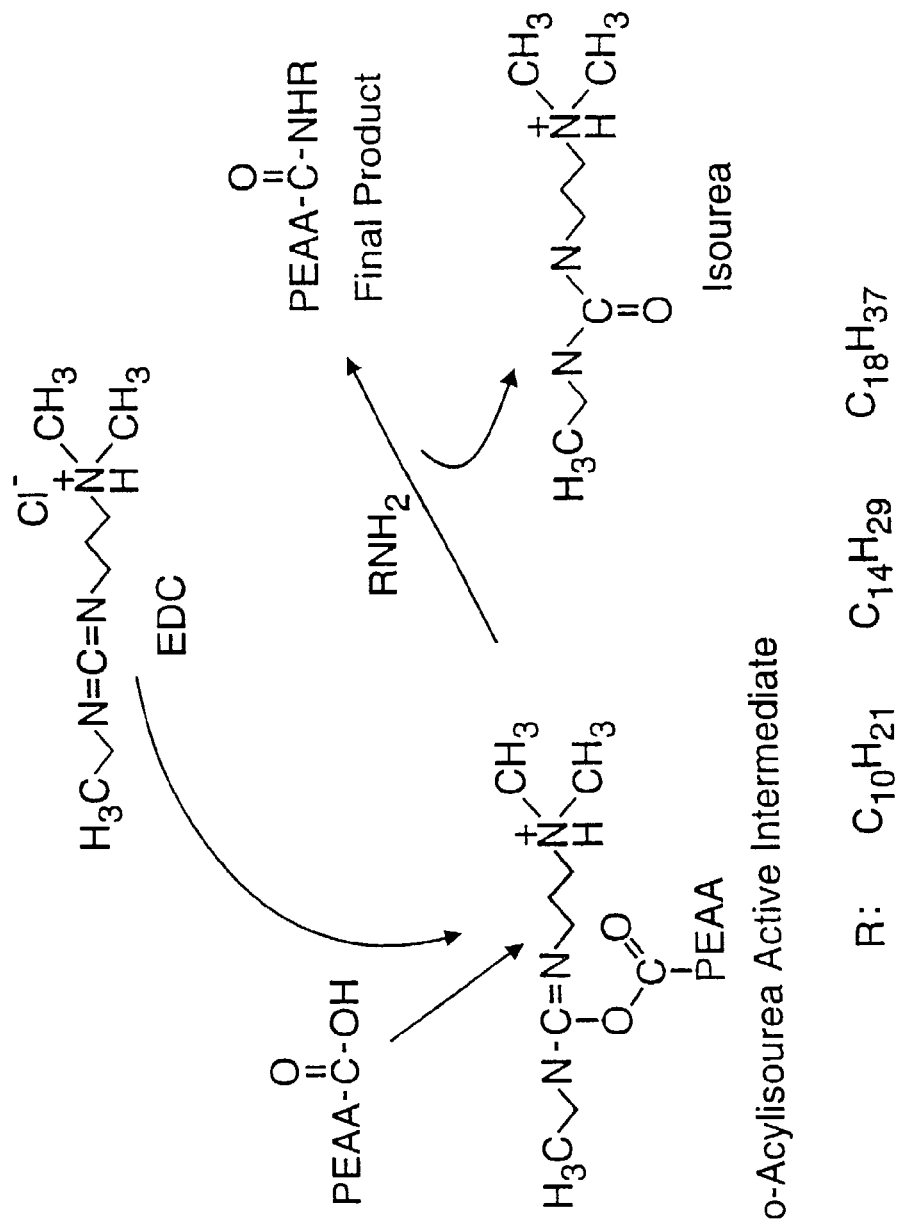
FIG. 1 illustrates a reaction mechanism involved in the process of synthesizing PEAA and alkylamine in the presence of EDC.

I. Glossary
II. General Overview
III. Methods of Preparing Liposomes
IV. Loading the Liposomes
V. Use of Liposomes for Drug Delivery
VI. Use of Liposomes as Diagnostic Agents
VII. Pharmaceutical Preparation
VIII. Examples I. Glossary As used herein, the term "alkyl" denotes branched or unbranched hydrocarbon chains, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "alkylene" refers to a divalent alkyl as defined above, such as methylene (—CH$_2$—), propylene (—CH$_2$CH$_2$CH$_2$—), chloroethylene (—CHClCH$_2$—), 2-thiobutene —CH$_2$ CH(SH)CH$_2$CH$_2$, 1-bromo-3-hydroxyl-4-methylpentene (—CHBrCH$_2$CH(OH)CH(CH$_3$) CH$_2$—), and the like.

The term "alkenyl" denotes branched or unbranched hydrocarbon chains containing one or more carbon—carbon double bonds.

The term "acyl" refers to a radical produced from an organic acid by removal of the hydroxyl group. Examples of acyl radicals include, but are not limited to, acetyl, pentanoyl, palmitoyl, stearoyl, myristoyl, caproyl, and oleyl.

The term "aryl" denotes a chain of carbon atoms which form at least one aromatic ring having preferably between about 6–14 carbon atoms, such as phenyl, naphthyl, indenyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "lipid" refers to a group of organic compounds that are esters of fatty acids and that are characterized by being insoluble in water, but soluble in many organic solvents. They are usually divided into at least three classes: (1) "simple lipids" which include fats and oils as well as waxes; (2) "compound lipids" which include phospholipids and glycolipids; and (3) "derived lipids" such as steroids.

The term "amphipathic lipids" include both a hydrophobic and hydrophilic aspect. Amphipathic lipids include, but are not limited to, phosphoglycerides and sphingolipids, phosphatidylcholine, phosphatidylethanolamine, phosphatidylserine, phosphatidylinositol, phosphatidic acid, palmitoyloleyl phosphatidylcholine, lysophosphatidylcholine, lysophosphatidylethanolamine, dipalmitoylphosphatidylcholine, dioleylphosphatidylcholine, distearoylphosphatidylcholine or dilinoleoylphosphatidylcholine.

The term "neutral lipids" refers to any number of lipid species that exist either in an uncharged or neutral zwitterionic form at physiological pH. Such lipids include, but are not limited to, diacylphosphtidylcholine, diacylphosphatidylethanolamine, ceramide, cephalin, cerebosides, and sphingomyelin.

The term "non-cationic lipids" refers to any neutral lipids or anionic lipids. Examples include, but are not limited to, cardiolipin, diacylphosphatidylserine and diacylphosphatidic acid.

The term "anionic charged lipids" refers to lipids such as dipalmitoyl glycero-3-(phospho-L-serine), dipalmitoyl-sn-glycero-3-phosphate and 1,2, dioleyl-sn-glycero-3-phospho-ethanolamine-N-(succinyl).

The term "cationic lipid" refers to a lipid species that carrries a net positive charge at physiological pH. Such lipids include, but are not limited to, DODAC, DOTMA, DDAB, DOTAP, DC-Chol, DMRIE, DODAP and DODMA.

Also, a number of commercially available preparations can be used with the present invention. These include, for example, LIPOFECTIN® (commercially available cationic liposomes comprising DOTMA and DOPE, available from GIBCO/BRL, Grand Island, N.Y., USA); and TRANSFECTAM® (available commercially from Promega Corp., Madison, Wis., USA; which comprises DOGS in ethanol); LIPOFECTAMINE® (commercially available cationic liposomes comprising DOSPA and DOPE from available commercially from GIBCO/BRL, Grand Island, N.Y., USA); LIPOFECTACE® (available commercially from GIBCO/BRL, Grand Island, N.Y., USA comprising DDAB and DOPE); 1,2-dioleyloxy-3(N,N,N-trimethylamino)propane chloride, or DOTAP, see, Stomatatatos, et al. Biochemistry 27:3917–3925 (1988)); N-(1-(2,3-Dioleoyloxy)propyl)-N,N,N-trimethylammonium methyl sulfate (DOTAP), available commercially from Boehringer Mannheim; 1,3-di-oleoyloxy-2-(6-carboxy-spermyl)-propylamide (DOSPAR), available commercially from Boehringer Mannheim. Both DOTAP and DOSPER contain internal ester bonds, considered to have lower cytoxic effects on transfected cells and to be degraded by endogenous esterases or lipases. The group also includes glycerol-based lipids (see, Leventis, et al, Biochem. Biophys. Acta 1023:124 (1990); lipolyamines (see, Behr, et al., U.S. Pat. No. 5,171,678), and cholesterol-based lipids (see, Epand, et al., WO 93/05162).

The term "fusogenic" refers to the ability of a liposome or other drug delivery system to fuse with membranes of a cell. The membranes can be either the plasma membrane or membranes surrounding organelles, e.g., endosome, nucleus, etc. "Fusogenesis" is the fusion of a liposome to such a membrane. Related to "fusogenic" are terms such as permeable, permeabilized, destabilized or unstable. These latter terms refer to the drug delivery system ability to release its payload at the site of interest.

The term "ligand" includes any molecule, compound or device with a reactive functional group and includes lipids, for example, amphipathic lipids, carrier compounds, bioaffinity compounds, biomaterials, biopolymers, biomedical devices, analytically detectable compounds, therapeutically active compounds, enzymes, peptides, proteins, immune stimulators, radiolabels, fluorogens, biotin, drugs, haptens, DNA, RNA, polysaccharides, liposomes, virosomes, micelles, immunoglobulins, functional groups or toxins. The foregoing list is not intended to be exhaustive.

The term PEAA refers to a polymer of 2-ethylacrylic acid. PEAA is polyelectrolyte, wherein the acid functionality can be used to covalently attach lipids that result in a hydrophobic anchor. When the PEAA has a covalently attached lipid, it is known as a "Lipo-PEAA". PEAA has the following formula

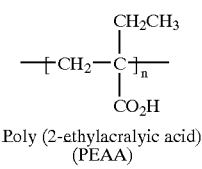

Poly (2-ethylacralyic acid)
(PEAA)

The molecular weight of each 2-ethylacrylic acid monomer is 100 grams/mole. Therefore, the number of units of a PEAA polymer (i.e., the index "n") can be calculated by dividing the polymer molecular weight by 100 to determine the percentage of units.

The polymeric PEAA can be derivatized with a lipid to generate a LipoPEAA. The percentage of Lipo-PEAA derivatized by a lipid is calculated by dividing the mole number of the lipid anchor (m) by the unit mole number of the PEAA (n) as schematically described below:

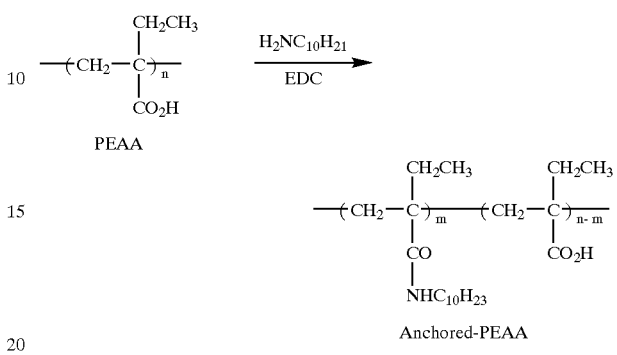

Anchored-PEAA

The term "diacylglycerolyl" denotes 2-fatty acyl chains, having independently between 2 and 30 carbons bonded to the 1- and 2-position of glycerol by ester linkages. The acyl groups can be saturated or have varying degrees of unsaturation. Diacylglycerolyls have the following general formula:

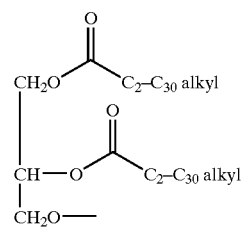

The term "dialkylglycerolyl" denotes two $C_1$–$C_{30}$ alkyl chains bonded to the 1- and 2-position of glycerol by ether linkages. Dialkylglycerolyls have the following general formula:

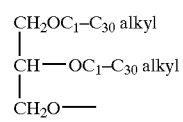

The term "1,2-diacyloxy-3-aminopropane" denotes 2-fatty acyl chains $C_{1-30}$ bonded to the 1- and 2-position of propane by an ester linkage. The acyl groups can be saturated or have varying degrees of unsaturation. The 3-position of the propane molecule has a —NH— group attached. 1,2-diacyloxy-3-aminopropanes have the following general formula:

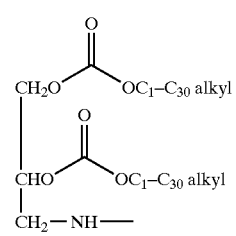

The term "1,2-dialkoxy-3-aminopropane" denotes 2-alkyl chains ($C_1$–$C_{30}$) bonded to the 1- and 2-position of propane by an ether linkage. The 3-position of the propane molecule has a —NH— group attached. 1,2-dialkoxy-3-aminopropanes have the following general formula:

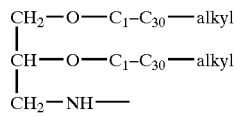

II. General Overview

A. Compounds and Synthesis

In one aspect, the present invention relates to compounds having the following general formula:

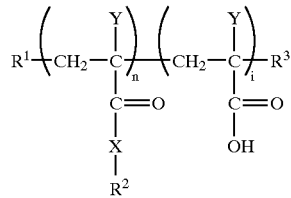

wherein $R^1$ Y, X, $R^2$, $R^3$, n and i are as defined above.

Compounds of Formula I are, in some instances, acylated derivatives of a hydrophobic polyanionic PEAA polymer chemically link to a lipid. Examples of chemical linkages which can be formed between the PEAA polymer and the lipid include, but is not limited to, ester bond linkages, sulfide bond linkages, and amide bond linkages. Additional types of chemical coupling chemistry known to those of skill in the art can also be used in the present invention. Such chemical coupling chemistries include, for example, radical polymerization, end functionalization via a chain transfer reagent, modification of functional radical initiator and post treatment of radical initiator fragment, such as hydrogenation of the cyano group in the polymer. In a preferred embodiment, the PEAA polymer is terminally-linked to a lipid through an amide bond using an anionic polymerization method, or alternatively, the PEAA polymer is linked to a lipid at various sites along the length of the PEAA polymer using a random point method.

In accordance with certain aspects of this invention, there are preferred embodiments of the compounds of Formula I. In one embodiment, a lipid, or mixtures thereof, are covalently linked to the PEAA polymer via an optionally substituted amino function. In this aspect, Y is hydrogen, optionally substituted $C_1$–$C_4$ alkyl, optionally substituted $C_5$–$C_6$ cycloalkyl and optionally substituted phenyl; X is optionally-substituted amino; $R^2$ is $C_6$–$C_{26}$ alkyl and $C_6$–$C_{26}$ alkenyl; and n and i added together have a sum of about 40 to about 250.

In accordance with other aspects of this invention, X is a carbon single bond and $R^2$ is dialkylglycerolyl, dialkenylglycerolyl, diacylglycerolyl and 1,2-diacyl-sn-glycero-3-phosphoethylenyl.

In accordance with certain other aspects of this invention, the lipid are covalently linked to the PEAA polymer via an ester linkage. In this aspect, Y is hydrogen, optionally-substituted $C_1$–$C_4$ alkyl, optionally-substituted $C_5$–$C_6$ cycloalkyl and optionally-substituted phenyl; X is a carbon single bond; $R^2$ is dialkylglycerolyl, dialkenylglycerolyl and diacylglycerolyl.

In addition to X being an optionally substituted amino, an oxygen atom, and a carbon single bond, other preferred embodiments are when X is a sulfur atom which generates a thio ester linkage between the PEAA and the lipid.

In Formula I, there are two sets of parentheses between $R^1$ and $R^3$. There is an "n" set and an "i" set, each of which define a monomeric unit. The definitions of Y, X and $R^2$ may vary from monomer to monomer for any given value of "n" and "i" monomers. The definition of Y can be different in the "n" monomer versus the "i" monomer. In addition, the definition of Y can vary within the "n" monomers and within the "i" monomers. For instance, in every other monomer "n", Y can have a different definition. This definition can be the same or it can be different than the definition of Y in the "i" monomer.

In connection with Formula I, it is important to note that although $R^1$ and R3 have been defined with the most likely functional groups present, it is possible that the radical species which initiates the polymerization reaction can also be present. As will be apparent to one skilled in the art, these functional groups represent such a small percentage of the entire compound that they are not easily identified. As such, in most instances, the end group on the resulting polymers are by convention not identified. However, in order to be complete, it is possible that $R^1$ and $R^3$ are generated via a combination polymerization method, or a disproportionation polymerization mechanism. If for example, 2,2'-azobis (isobutylnitrile) were used as the initiator, $R^1$ and $R^3$ could be isobutylnitrile or a methylene group. If chain transfer agents were used to terminate the polymeric chains, $R^1$ and $R^3$ can be a diphenylhexyl or diphenylpropyl group. Other radical initiators and chain transfer agents will be known to those skilled in the art. Depending on the radical initiator or chain transfer agent used, the end groups i.e., $R^1$ and $R^3$, can have the initiator fragment as their identity. As such, $R^1$ and $R^3$ include all such radical initiators and chain transfer agents.

As will be readily apparent to those of skill in the art, anionic polymerization can also produce various $R^1$ and $R^3$ groups. These groups include, but are not limited to, functional initiators or functional terminating agents, as well as groups such as alkyl, aromatic groups, hydroxyl, thiol, amino, alcohols, such as methanol; acids, such as acetic acid; and water. As such, $R^1$ and $R^3$ include all such groups.

Moreover, the hydrophobicity of the Y group appears to play an important role in the pH-dependent destabilization of the membrane bilayer which leads to the release of the liposome's content and/or fusion of the liposome. A more hydrophobic Y group tends to facilitate polymer insertion into the membrane as a function of pH. This results in a membrane destabilization at higher pHs compared to a group Y with lower hydrophobicity. For example, when Y is a methyl group a lower pH is required for membrane disruption than when Y is an ethyl group. When Y is alkyl, the pH required for disruption of the membrane increases in the order of alkyl chain length. Therefore, it is possible to control the pH sensitivity of the polymer by altering the hydrophobicity of the Y group. In addition, it is possible to alternate the hydrophobicity of Y within the polymer. For instance, a more hydrophobic group in every other monomer, every third monomer, or every fourth monomer, etc., can change the pH sensitivity of the membrane at a given pH. Moreover, the hydrophobicity of the Y group determines in part, the size of the polymer required to destabilize the membrane.

In connection with the above compounds, the present invention provides methods for making lipid derivatives of a polyelectrolyte, i.e., poly(2-ethylacrylic acid). As described above, PEAA can be chemically linked to a lipid to form a lipo-polyelectrolyte having a hydrophobic anchor i.e., Lipo-PEAA, using several methods. Two examplar methods include the random point method and the anionic polymerization method. For instance, in order to generate a Lipo-PEAA using the random point procedure, a coupling reaction, such as a 1-(3-dimethylaminopropyl)-3-ethylcarbodiimide hydrochloride (EDC) mediated reaction, can be used. In this procedure, PEAA is used with a suitable amine, such as 1-decylamine [$CH_3(CH_2)_9NH_2$], dissolved in water (pH about 7.0). FIG. 1 illustrates the synthetic scheme that can be used to chemically link the PEAA and alkylamine in the presence of EDC using the random point method. As illustrated therein, poly(2-ethylacrylic acid) is mixed with the water-soluble carbodiimide (EDC) in the presence of water to form an O-acylisourea intermediate that is finally converted to the anchored PEAA.

The carbon chain length of the amine used will depend, in part, on the desired properties of the Lipo-PEAA. In a preferred embodiment, the lipid is an alkylamine with carbon chain lengths in the range of about $C_{-6}$ to about $C_{-22}$ and, more preferably, from about $C_{-10}$ to about $C_{-18}$. The alkylamine can be saturated or unsaturated. In one preferred embodiment, the alkylamine is saturated. If the alkylamine is unsaturated, the bonds can be cis or trans. In other embodiments, the lipid is a mixture of alkylamines such as saturated and unsaturated alkylamines. The PEAA and alkylamine are dissolved in water and EDC is slowly added.

The level or amount of alkylamine can be monitored during the reaction by a number of different analytical techniques, including thin layer chromatograph (TLC). After the reaction is complete, the resultant derivative can be precipitated by adjusting the pH of the solution from pH 2 to about pH 3. The pellets can then be separated and redissolved in an alkali solution, such as 2 M sodium hydroxide (NaOH) solution, and then stirred. The mixture can then be centrifuged and the pellets can be separated and washed in water and lyophilized. An illustration of a Lipo-PEAA produced by the random point method is set forth below.

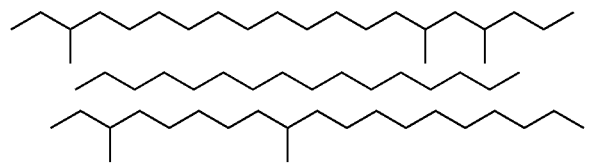

As the name implies, the lipid anchors are randomly distributed on the PEAA polymer and, as such, the illustration above is merely one example of a randomly distributed lipid anchor.

Figure 2:
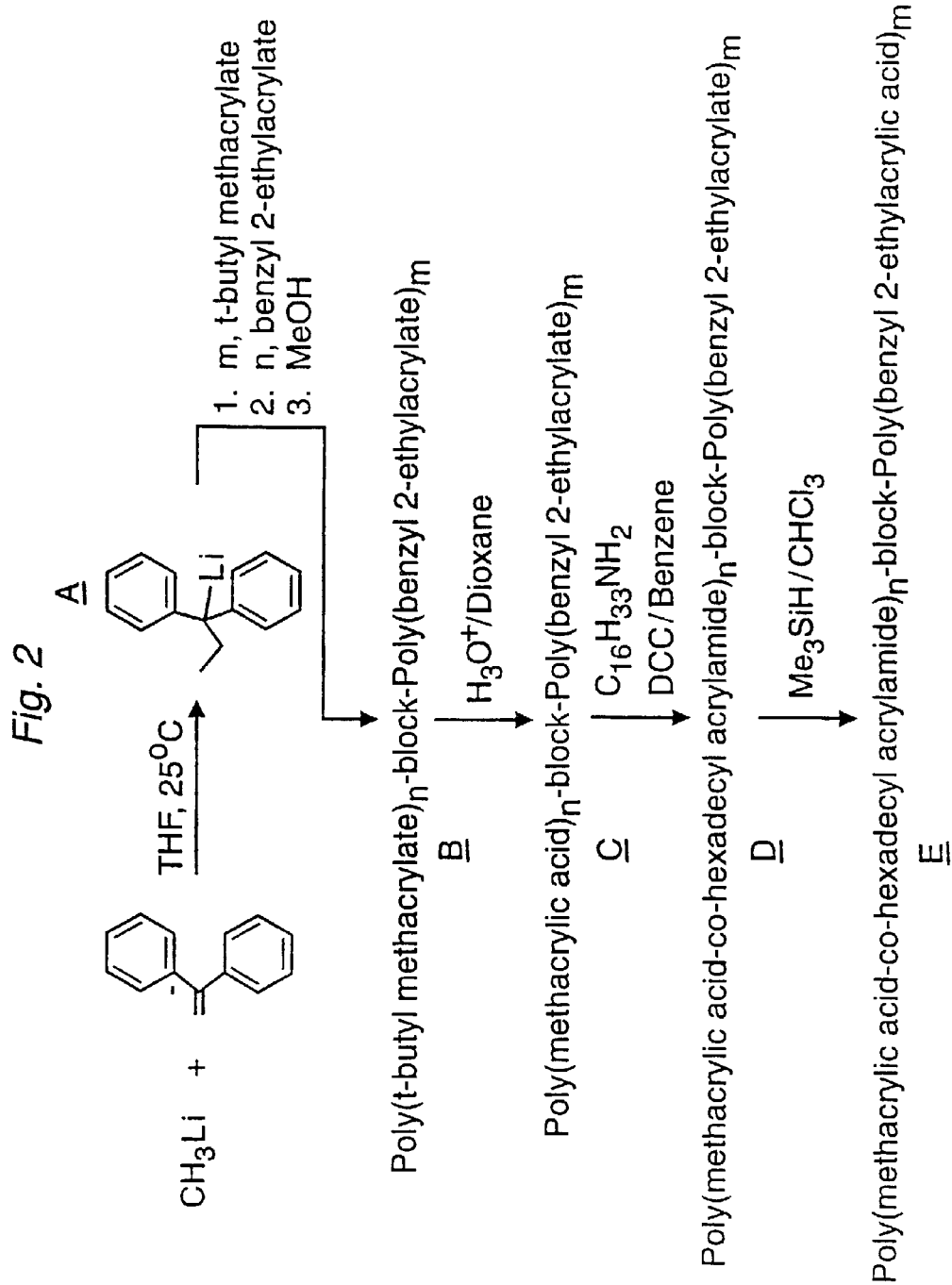
FIG. 2 is a schematic diagram of the synthesis of poly(2-ethylacrylic acid) bearing terminal hydrophobic anchors using an anionic polymerization method.

In addition to the random point method, the present invention provides methods for preparing a terminally-linked anchored PEAA. In one preferred method, derivatives of PEAA can be chemically linked to a lipid to form a Lipo-PEAA, wherein the lipid can form a lipid anchor, using anionic polymerization. FIG. 2 illustrates the anionic polymerization method using t-butyl methacrylate and benzyl 2-ethylacrylate. This reaction is carried out using 1,1-diphenypropyl-lithium as an initiator in a solvent, such as tetrahydrofuran (THF) at −78° C.

More particularly, in this method, 1,1-diphenylpropyl-lithium is prepared using freshly prepared 1,1-diphenylethylene and methyllithium. Poly(t-butyl methacrylate)-block-poly(benzyl-2-ethylacrylate) can then be prepared using a reactor charged with argon and the freshly distilled 1,1-diphenylpropyllithium as the initiator. The reactor contents are then stirred continuously and the temperature is maintained at about −78° C. Next, the monomer t-butyl methacrylate (tBMA) is introduced slowly over a 1–2 minute period and thereafter benzyl 2-ethylacrylate (BzEA) is added and reaction is allowed to proceed to completion. The polymerization mixture can then be quenched with the addition of methanol. The polymer is separated by filtration and redissolved in THF and precipitated into methanol. Subsequent drying in a vacuum oven at 30° C. for 24 hours yields poly(t-butyl methacrylate)-block-poly(benzyl 2-ethyl acrylate).

The poly(methacrylic acid)-block-poly(benzyl 2-ethylacrylate), the poly(t-butyl methacrylate)-block-poly(benzyl 2-ethylacrylate) formed above dissolve in a mixture of 1,4-dioxane and 10% hydrochloric acid. After heating, the polymer is precipitated in methanol and can be isolated by filtration.

Finally, the terminally-linked lipid-anchored PEAA (in this instance, poly(methacrylic acid-co-hexadecyl acrylamide)-block-poly(benzyl 2-ethylacrylate)) can be formed using the poly(methacrylic acid)-block-poly(benzyl 2-ethylacrylate) and hexadecylamine using a 1,3-dicyclohexylcarbodiimide mediated coupling reaction and subsequent removal of the benzyl ester using iodotrimethylsilane. An illustration of a Lipo-PEAA which is termally-anchored is shown below.

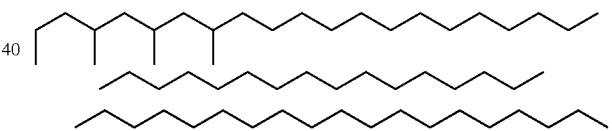

One of the advantages of the pH-sensitive polyanionic polymers of the present invention is that they can be synthesized in a controlled manner to produce defined sizes and, thus, one can readily control their pH sensitivity. This is an important advantage over the methods used in the prior art which usually resulted in a mixture of polymers having different chain lengths. One drawback of such heterogenous chain length populations is that the number of carboxyl groups on the Lipo-PEAA will vary between different preparations. This variation will cause fluctuations in the properties of the resulting systems and, in turn, in inconsistencies in the final products. Accordingly, unlike previous prior art methods, the present invention provides methods for synthesizing hydrophobic Lipo-PEAA that are more homogeneous.

In still another embodiment, further modification can be done on the PEAA by derivatizing the linkage on one end with a molecule bearing a steric hindrance functional group, such as polyethylene glycol, ATTA (see, U.S. patent application Ser. No. 09/218,988, filed Dec. 22, 1998, incorporated herein by reference) or some other ligand, while the other end of the PEAA is chemically linked to a lipid or ligand. The attachment can be a single linear attachment, or the attachment can be a brushlike attachment.

In one embodiment, ATTA can be linked to PEAA. The ATTA compound has the following general formula:

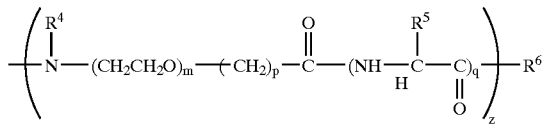

In Formula II, $R^4$ is a member selected from the group consisting of hydrogen and alkyl; $R^5$ is a member selected from the group consisting of hydrogen, optionally-substituted alkyl, optionally-substituted aryl and a side chain of an amino acid; $R^6$ is a member selected from the group consisting of hydrogen, halogen, hydroxy, alkoxy, mercapto, hydrazino, amino, $NR^7R^8$, wherein $R^7$ and $R^8$ are independently hydrogen or alkyl, and a ligand; z is 4 to 80; m is 2 to 6; p is 1 to 4; and q is 0 or 1.

Either PEAA or a hydrophilic polymer attached to PEAA (e.g., polyethylene glycol or ATTA) can have a ligand covalently attached to it. The ligand can be covalently attached to the PEAA polymer, the hydrophilic polymer, or both. Suitable ligands include, but are not limited to, lipids, amphipathic lipids, carrier compounds, bioaffinity compounds, biomaterials, biopolymers, biomedical devices, analytically detectable compounds, therapeutically active compounds, enzymes, peptides, proteins, immune stimulators, radiolabels, fluorogens, biotin, drugs, haptens, DNA, RNA, polysaccharides, liposomes, micelles, immunoglobulins, functional groups or toxins. Antibodies of various classes and subclasses and various specificity can also be used as ligands. Suitable biomaterials include, but are not limited to, stents, catheters and other devices.

Methods known to those of skill in the art can be used for covalent attachment of ligands to PEAA, ATTA or the hydrophilic polymer (e.g., PEG, ATTA, etc.). Suitable linkages include, but are not limited to, amide, amine, carboxyl, carbonate, carbamate, ester and hydrazone bonds. Additional linkages, such as phosphoro and disulfide bonds, can be employed if a cross-linker is used. It will be apparent to those skilled in the art that the ligand(s) to be attached must have a complementary functional group with the PEAA or hydrophilic polymer. The reaction of these two groups, one on the ligand and the other on the PEAA or hydrophilic polymer will provide the desired linkage.

A convenient method to attach proteins to a PEAA polymer or other hydrophilic polymer is via a carbamate linkage. U.S. Pat. No. 5,324,844, incorporated herein by reference, describes the use of the functional group succinidyl carbonate to attach proteins, and this method is also applicable to the compounds described herein.

It will be immediately obvious to a person skilled in the art that conventional peptide chemistry which results in either activation or protection of amino and carboxylic acid groups is applicable herein (see, e.g., Bodansky, M., et al., *Principles of Peptide Synthesis,* 2nd Edition, Springer-Verlag Inc., New York (1993)). By using these conventional procedures, selective protection and activation of either side of the PEAA or ATTA can be accomplished.

The polyelectrolytes, i.e., PEAA polymers, in the present invention are polymers bearing functional groups that are titratable from the charged form to an uncharged form, or, alternatively, from the uncharged to a charged form. In the present invention, the charged form is preferred when at physiological pH. Although the synthetic description above details the generation of pH-sensitive polymers having proton titratable functional groups, such as carboxylic acids, as in poly(α-ethylacrylic acid), other examples of titratable functional groups that can exist in the pH-sensitive polymers of the present invention include, but are not limited to, phosphoric acids, phosphonic acid, phosphinic acid, sulfonic acids, sulfuric acids, alcohols, amines, thiols, imides, and the like. For the present invention, carboxylic acids are preferred. In addition to the acids, esters and salts of the acids can be used in the present invention, including carboxylic acid esters, sulfonates, etc.

In one embodiment, the poly(2-ethylacrylic acid)s have a molecular weights ranging from about 1,200 to about 25,000. In a more preferred embodiment, the poly(2-ethyacrylic acid)s have molecular weights ranging from about 4,200 to about 25,000 and, more preferably, from about 8,400 to about 20,000. Generally, it has been found that increasing the molecular weight of the poly(2-ethylacrylic acid)s increases the pH sensitivity of the polyelectrolyte.

The versatility of the synthesis of Lipo-PEAA allows for varying the chain lengths of the alkylamine. As has been discussed, the lipid portion of the Lipo-PEAA can have various modifications. For instance, the chain length can be varied. The number of chains and the degree of saturation versus unsaturation can be varied. In addition, the kind and amounts of lipids can vary. The present invention includes all such permeations and variations. Table 1 sets forth a list of compounds wherein the lipid chain lengths and the molecular weight of the PEAA have been varied.

It will be apparent to those skill in the art that by changing the molecular weight of the PEAA, the lipid percentage can be adjusted and optimized accordingly.

TABLE 1

The synthesized Lipo-poly(ethylacrylic acid)s.

| Compound | PEAA Mol. Weight | Lipid Length | Anchor Percentage (%) |
|---|---|---|---|
| 1 | 20,000 | C10 | 0 |
| 2 | 20,000 | C10 | 3 |
| 3 | 20,000 | C10 | 5 |
| 4 | 20,000 | C10 | 7 |
| 5 | 8400 | C10 | 0 |
| 6 | 8400 | C10 | 3 |
| 7 | 8400 | C10 | 5 |
| 8 | 8400 | C10 | 7 |
| 9 | 8400 | C14 | 3 |
| 10 | 8400 | C14 | 5 |
| 11 | 8400 | C14 | 7 |
| 12 | 8400 | C18 | 3 |
| 13 | 8400 | C18 | 5 |
| 14 | 8400 | C18 | 7 |

Both the terminally-linked and random point methods result in the production of a series of new hydrophobic lipid anchors or derivatives, known as "Lipo-poly(2-ethylacrylic acid)" or "Lipo-PEAA," having defined sizes. FIG. 14 illustrates the use of Lipo-PEAA in the present invention.

Any lipid can be coupled to the PEAA polymer of the present invention. For instance, lipids which can be coupled to PEAA are those which adopt a non-lamellar phase under physiological conditions or under specific physiological conditions, but which are capable of assuming a bilayer structure in the presence of a bilayer stabilizing component under physiological conditions or near alkaline conditions. Such lipids include, but are not limited to, alkylamines, fatty alcohols, cholesterol, phosphatidylethanolamine, glycerol-based phospholipids, sphingosine based lipids, glycolipids and mixtures thereof. Alkylamine lipids are preferred. Other lipids known to those of skill in the art to adopt a non-bilayer structure under physiological conditions can also be used to form Lipo-PEAA of the present invention. Alternatively, other bilayer-forming lipids, such as dioleylphosphotidylcholine (DOPC), can also be coupled to the PEAA polymers of the present invention. It will be readily apparent to those skilled in the art that additional lipids such as cationic, neutral and amphipathic lipids, will also be suitable for coupling to the PEAA polymers. In addition, the foregoing lipids can be used in the formulation of the lipid-based delivery systems without the PEAA attached.

As will be described in more detail below, by varying the composition, concentration and the percentage of the lipid which is coupled to the PEAA, it is possible to control the rate of fusion or release of the encapsulated bioactive compound upon encountering an environment with a lower pH than the physiological pH. One of ordinary skill in the art will appreciate that the concentration of the lipid can be varied depending on the size of the polymeric polyelectrolyte component used. This will determine the rate at which the liposome becomes pH-sensitive and, in turn, fusogenic, permeabilized or destabilized.

In one embodiment of the present invention, the amount of lipid coupled to the PEAA polymer varies between about 1 percent and about 10 percent. When using an alkylamine (such as $C_{10}H_{21}NH_2$) as the lipid chemically linked to the PEAA (MW 20,000), the lipid can vary from about 1 percent to about 7 percent. The preferred concentration of the alkylamine ($C_{10}H_{21}NH_2$) anchored to the PEAA is about 3 percent. The PEAA polyelectrolyte polymers can be designed such that they can be readily conjugated to a lipid at one terminal end and/or to a targeting ligand or other agent at the other end.

B. Method of Incorporation into Liposomes

Once formed, the pH-sensitive polymers of the present invention can be incorporated into or covalently attached to liposomes, lipid particles, a micelle, a virosome, a lipid-nucleic acid particle or other lipid carrier systems using methods known to and used by those of skill in the art. More particularly, the Lipo-PEAAs of the present invention can be associated with the lipid vesicle, lipid particles or other lipid carrier systems using various methods to form a pH-sensitive delivery vehicle. For instance, the Lipo-PEAA derivatives are hydrophobic which, in turn, allows the lipid-anchor to efficiently incorporate into the membrane lipid bilayer of the liposome.

In the following embodiment, the discussion refers generally to "liposome" and the various ways in which the Lipo-PEAAs can be incorporated into liposomes. However, as will be apparent to those skilled in the art, other lipid-based delivery systems are also applicable. Such delivery systems include, but are not limited to, lipid particles, micelles, virosomes and lipid-nucleic acid particles.

Depending on the method employed to form the liposome, the Lipo-PEAA can be incorporated onto the outer surface of the liposome or on the outer and inner surfaces of the liposome. For instance, the Lipo-PEAA is incorporated onto the surface of the lipid bilayer of the liposome by incubating the Lipo-PEAA with preformed liposomes using the coating method as described hereinbelow. Alternatively, the Lipo-PEAA is incorporated onto the surface of the lipid bilayer of the liposomes using a co-extrusion method.

Without being bound by theory, it is believed that the Lipo-PEAA derivative when incorporated into the bilayer of the liposome forms a lipid carrier that can release its contents by becoming permeable, destabilized or fusogenic in acidic pH conditions. This pH-sensitive liposome, upon encountering an acidic environment, results in a conformational collapse of the polyelectrolyte. As a result of the collapse, the polyelectrolyte interacts with the surface of the liposome and destabilizes the organizational structure of the liposome such that the liposome adopts a non-bilayer intermediate structure, which can lead to destabilization of the membrane and to fusion or release of the payload.

These pH-sensitive liposomes are advantageous because they can be used in an environment with a pH lower than physiological pH, such as in sites of primary tumors, metastasis, inflammation and infection (see, Nayar, et al., "Potential applications of pH-sensitive liposomes as drug delivery systems" in *Liposomes as Drug Carriers*, p. 771–782 (1988)).

As described above, Lipo-PEAA derivatives can be incorporated into the lipid bilayer thereby forming a pH-sensitive fusogenic liposome. However, the present methods also includes free PEAA being encapsulated into the liposomes.

Lipids suitable for use in the drug delivery systems include lipids such as phosphoglycerides, sphingolipids, phosphatidylcholine, phosphatidylethanolamine, anionic lipids, cationic lipids, non-cationic lipids, neutral lipids, lipolyamines, and cholesterol-based lipids. For the present invention, phosphatidylcholine is preferred. Such phosphatidylcholines are commercially available or can be isolated or synthesized using conventional techniques known to those skilled in the art. Suitable phosphatidylcholines include, but are not limited to, the following: distearoylphosphatidylcholine (DSPC), dipalmitoylphosphatidylcholine (DPPC), dimyristoylphosphatidylcholine (DMPC), dilauroylphosphatidylcholine (DLPC), dioleylphophatidylcholine (DOPC), hydrogenated egg phosphatidylcholine, soy phosphatidylcholine, hydrogenated soy phosphatidylcholine, and egg phosphatidylcholine (EPC).

It will be readily apparent to those skilled in the art that there is overlap between the lipids that can be used to form the lipid-based delivery systems and the lipids that can be attached to the PEAA polymer. For instance, phosphatidylcholines, which have a variety of acyl chain groups of varying chain lengths and degrees of saturation, can be conjugated to poly(2-ethylacrylic acid)s to form pH-sensitive liposomes. Further, phosphatidylcholines with mono- or di-unsaturated fatty acids and mixtures of saturated and unsaturated fatty acids can be covalently attached to PEAA.

In accordance with one embodiment of the present invention, the formation of a pH-sensitive liposome can be stabilized in a bilayer structure by bilayer stabilizing components which are either bilayer forming themselves, or are of a complementary dynamic shape. It is important to select a bilayer stabilizing component capable of exchanging out of the liposome or of preventing leakage in the bilayer. Examples of suitable bilayer stabilizing components include, but are not limited to, lipids, lipid-derivatives, detergents, proteins, polyethylene glycol, ATTA and peptides. In a preferred embodiment, the bilayer stabilizing component is cholesterol.

The pH-sensitive liposomes of the present invention trigger fusion, release or both, of the encapsulated bioactive compound when protonation of the amphiphilic titratable group occurs upon encountering an environment having a pH lower than a neutral or physiological pH. Thus, in one embodiment, the present invention includes pH-sensitive liposomes wherein the rate at which the liposome becomes permeable, unstable or fusogenic can be controlled by pH.

The rate at which the liposome becomes fusogenic can be varied over a pH range of about 3 to about 10. Preferably, the rate at which the liposome becomes fusogenic can be varied over a pH range of about 3 to about 8 and, more preferably, over a pH range of about 5 to about 7. In accordance with certain aspects of this invention, the pH-sensitive liposomes are stable at physiological or near alkaline pH, i.e., from about pH 7.0 to about pH 8.0, and they become unstable at a pH range from about 4.0 to about 6.2 with a greater than 80 percent release of entrapped payload.

In one embodiment, when the liposome is to be fusogenic, the Lipo-PEAA is formulated with a phosphatidylcholine, cholesterol and a bilayer stabilizing component. In one preferred embodiment, egg phosphatidylcholine (EPC), dimyristoylphosphatidylcholine (DMPC), dipalmitoylphosphatidylcholine (DPPC) or distearoylphosphatidylcholine (DSPC) can be used. For the present invention, egg phosphatidylcholine (EPC) and cholesterol are used. The Lipo-PEAA can be incorporated into the formulation so that it is on the outside of the liposome using the coating reaction described herein. Alternatively, the Lipo-PEAA can be incorporated into the liposome to be on the outside or the inside or both outside and inside, using the co-extrusion method (see, Hope, M., et al., Biophys. Acta, 812:55–65 (1985)).

In another embodiment, an acylated derivative, such as an acyl amine, is synthesized to enhance the fusogenic ability of the liposome by incorporating into the liposome. In yet another embodiment, the Lipo-PEAA can be inserted into vesicles which results in intracellular delivery of the vesicle's contents.

In another embodiment, the free PEAA polymer can exclusively be within the interior of the liposome. For example, polymeric PEAA having a molecular weight of about 8000 can be encapsulated in a liposome consisting essentially of 1-2-oleyl-sn-phosphatidylcholine (POPC) and cholesterol (Chol).

C. Liposomes

In certain other aspects, this invention relates to a pH-sensitive liposome, comprising a lipid and a compound of the Formula I. In other aspects, the pH-sensitive liposome is fusogenic. In other aspects, the liposome becomes fusogenic, destabilized or permeablized and releases it payload. When forming a pH-sensitive liposome, the Lipo-PEAA is present at a final concentration of about 1 percent to about 22 percent of the Lipo-PEAA to lipid weight to weight (w/w). More preferably, the concentration of Lipo-PEAA is about 5 percent to about 15 percent (w/w) of Lipo-PEAA to lipid. In the present invention, 10 percent (w/w) Lipo-PEAA to lipid is preferred.

Liposomes are lipid bilayer membranes existing in one or more concentrically ordered form containing an entrapped aqueous volume. Liposomes can be unilamellar vesicles (onion-like structures characterized by multiple membrane layers, each separated from the next by an aqueous layer). The bilayer is composed of two lipid monolayers having a hydrophobic "tail" of lipid monolayers that orient toward the center of the bilayer while the hydrophilic (polar) "head" orient toward the aqueous volume. A variety of liposome types are known and include, for example, multilamellar vesicles (MLV's), single unilamellar vesicles (SUV's), large unilamellar vesicles (LUV's), stable plurilamellar vesicles (SPLV's), frozen and thawed multilamellar vesicles (FATMLV's), and reversed phase evaporation vesicles (REV's) as described in U.S. Pat. Nos. 5,049,392, 5,204,112 and 5,262,168, the teaching of which are incorporated herein by reference.

The polymorphic behavior of lipids in organized assemblies can be explained qualitatively in terms of the dynamic molecular shape concept (see, Cullis et al., in "Membrane Fusion" (Wilschut, J. and D. Hoekstra (eds.), Marcel Dekker, Inc., New York, (1991)). When the effective cross-sectional areas of the polar head group and the hydrophobic region buried within the membrane are similar, then the lipids have a cylindrical shape and tend to adopt a bilayer intermediate form. Cone-shaped lipids, which have polar head groups that are small relative to the hydrophobic component, such as unsaturated phosphatidylethanolamines, prefer non-bilayer phases such as inverted micelles or inverse hexagonal phase.

III. Methods of Preparing Liposomes

Several methods are available for preparing liposomes as described, for example, by Szoka, et al., Ann. Rev. Biophys. Bioeng., 467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Deamer and Bangham, Biochim. Biophys. Acta, 443:629–634 (1976); Fraley, et al., Proc. Natl., Acad. Sci., 85:242–246 (1988); Liposomes, Marc J. Ostro (ed.), Marcel Dekker, Inc., New York, (1983) Chapter 1; and Hope, et al., Chem. Phys. Lip., 40:89 (1986), all of which are incorporated herein by reference. Suitable methods include, for example, sonication, extrusion, high pressure/homogenization, microfluidization, detergent dialysis, calcium-induced fusion of small liposome vesicles, and ether fusion methods, all of which are well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids with more vigorous agitation or by adding solubilizing detergents such as deoxycholate.

Unilamellar vesicles are generally prepared by sonication or extrusion. Sonication is generally performed with a tip sonifier, such as a Branson tip sonifier, in an ice bath. Typically, the suspension is subjected to several sonication cycles. Extrusion can be carried out by biomembrane extruders, such as the Lipex Biomembrane Extruder. Defined pore size in the extrusion filters can generate unilamellar liposomal vesicles of specific sizes. The liposomes can also be formed by extrusion through an asymmetric ceramic filter, such as a Ceraflow Microfilter, commercially available from the Nortan Company, Worcester Mass.

Following their preparation, the liposomes can be sized to achieve a desired range and a relatively narrow distribution of liposome sizes. A size range of about 0.05 microns to about 0.20 microns allows the liposome suspension to be sterilized by filtration through a conventional filter, typically a 0.22 micron filter. The filter sterilization method can be carried out on a high throughput basis if the liposomes have been sized down to about 0.05 microns to about 0.10 microns.

Several techniques are available for sizing liposomes to a desired size. One sizing method is described in U.S. Pat. No. 4,737,323, incorporated herein by reference. Sonicating a liposome suspension by either bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.05 microns and 0.50 microns, are observed. In both of these methods, the particle size distribution can be monitored by conventional laser beam particle-size discrimination. In addition, the size of the liposomal vesicle can be determined by quasi-electric light scattering (QELS) as described in Bloomfield, *Ann. Rev. Biophys. Bioeng.* 10:421–450 (1980), incorporated herein by reference. Average liposome diameter can be reduced by sonication of formed liposomes. Intermittent sonication cycles can be alternated with QELS assessment to guide efficient liposome synthesis.

Extrusion of liposomes through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes can be extruded through successively smaller-pore membranes, to achieve a gradual reduction in liposome size. For use in the present invention, liposomes having a size from about 0.05 microns to about 0.5 microns are preferred.

IV. Loading the Liposomes

Methods of loading conventional drugs into liposomes include, for example, an encapsulation technique, loading into the bilayer, and a transmembrane potential loading method.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formulation of the liposome can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. No. 4,885,172, U.S. Pat. No. 5,059,421, and U.S. Pat. No. 5,171,578, the contents of which are incorporated herein by reference. Briefly, the transmembrane potential loading method can essentially be used with any conventional drug, which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes having different internal and external media and has an associated proton gradient. Drug accumulation can than occur in a manner predicted by the Henderson-Hasselbach equation.

V. Use of Liposomes as Drug Delivery Vehicles.

In other aspects, this invention relates to methods for delivering a therapeutic compound or drug to a target cell comprising administering to a host containing the target cell a pH-sensitive liposome comprising a lipid and a compound of the Formula I.

The drug delivery compositions of the present invention (e.g., liposomes, micelles, lipid-nucleic acid particles, virosomes, etc.) are useful for the systemic or local delivery of therapeutic or bioactive agents and are also useful in diagnostic assays. Such delivery systems are described herein in greater detail.

Further, these pH-sensitive and fusogenic liposomes can be used in mammalian cells that have a pH lower than the physiological pH. Such cellular environments include tumors, inflamed and infected regions, endosomes and lysosomes.

As discussed previously, the following discussion refers generally to liposomes; however, it will be apparent to those of skill in the art that this same discussion is fully applicable to other drug delivery systems of the present invention (e.g., micelles, virosomes, lipid particles, lipid-nucleic acid particles, etc.).

For the delivery of therapeutic or bioactive agents, the compositions can be loaded with a therapeutic agent and administered to the subject requiring treatment. The therapeutic agents that are administered using the present invention can be any of a variety of drugs that are selected to be an appropriate treatment for the disease or condition to be treated. Often the bioactive agent can be antimitotic agents (e.g., colchicine, anthracyclines and other antibiotics, folate antagonists and analogs, alkyl sulfonates), oligonucleotides, and DNA (sense or antisense), nucleic acid analogs, proteins, peptides, polyanionic drugs, plasmid DNA, ribozyme, chromosomal DNA.

Often the drug will be an antineoplastic agent, such as vincristine, doxorubicin, mitoxanthrone, campthothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It can also be desirable to deliver anti-infective agents to specific tissues by the present methods. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; antidepressants, e.g., imipramine, amitriptyline and doxepin; anti-convulsants, e.g., phenytoin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antigalucoma agents, vitamins, narcotics, and imaging agents. Other drugs which can be administered using the compositions and methods of the present invention will be readily apparent to those of skill in the art.

The drug delivery vehicles of this invention can also be loaded with nucleic acid, including but not limited to, DNA, RNA, antisense nucleic acid, cDNA, plasmid DNA, minichromosomes and ribozymes. These nucleic acids can be loaded using detergent dialysis as described in PCT publication WO 96/40964 and U.S. patent application Ser. No. 08/856,374, the teaching of which are incorporated herein by reference.

VI. Use of the Liposomes as Diagnostic Agents

In addition to being useful for drug delivery, the liposomes prepared using the compounds of this invention can also be labeled with markers that will facilitate diagnostic imaging of various disease states including tumors, inflamed joints, lesions, etc. Typically, these labels will be radioactive markers, although fluorescent labels can also be used. The use of gamma-emitting radioisotopes is particularly advantageous as they can easily be counted in a scintillation well counter, do not require tissue homogenization prior to counting, and can be imaged with gamma cameras.

Gamma- or positron-emitting radioisotopes are typically used, such as $^{99}Tc$, $^{24}Na$, $^{51}Cr$, $^{59}Fe$, $^{67}Ga$, $^{86}Rb$, $^{111}In$, $^{125}J$, and $^{195}Pt$ as gamma-emitting; and such as $^{68}Ga$, $^{82}Rb$, $^{22}Na$, $^{75}Br$, $^{122}I$, and $^{18}F$ as positron-emitting.

The liposomes can also be labeled with a paramagnetic isotope for purposes of in vivo diagnosis, as through the use of magnetic resonance imaging (MRI) or electron spin resonance (ESR). See, for example, U.S. Pat. No. 4,728,575, the teachings of which are incorporated herein by reference.

VII. Pharmaceutical Preparation

The liposome compositions of the present invention can be administered to a subject using standard methods and techniques known to those of skill in the art. Preferably, pharmaceutical compositions of the liposome are administered parenterally, which includes intraperitoneally, intravenously, subcutaneously and intramuscularly. More preferably, the pharmaceutical compositions are administered intravenously by a bolus injection. Suitable formulations for use in the present invention are found in Remington's Pharmaceutical Sciences, Mack Publishing Company, Philadelphia, Pa., 17th ed. (1985). The pharmaceutical compositions can be used, for example, to diagnose a variety of conditions or to treat a diseased state. The diseases include, but are not limited to, inflammation associated with rheumatoid arthritis, post-ischemic leukocyte-mediated tissue damage (reperfusion injury), acute leukocyte-mediated lung injury (e.g., adult respiratory distress syndrome), septic shock, and acute and chronic inflammation, including atopic dermatitis and psoriasis. In addition, various neoplasms and tumor metastases can be treated.

Preferably, the pharmaceutical compositions are administered intravenously. Thus, this invention provides compositions for intravenous administration that comprise a solution of the liposomes or other drug delivery system, suspended in an acceptable carrier, preferably an aqueous carrier. A variety of aqueous carriers can be used, e.g., water, buffered water, 0.9% isotonic saline, and the like. These compositions can be sterilized by conventional, well-known sterilization techniques, or can be sterile filtered. The resulting aqueous solutions can be packaged for use as is or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like; for example, sodium acetate, sodium lactate, sodium chloride, potassium chloride, calcium chloride, sorbitan monolaurate, triethanolamine oleate, etc.

In certain embodiments, it is desirable to target the liposomes, or other drug delivery system of this invention using targeting moieties that are specific to a cell type or tissue. Targeting of liposomes using a variety of targeting moieties, such as ligands, cell-surface receptors, glycoproteins, vitamins (e.g., riboflavin) and monoclonal antibodies, has been previously described (see, e.g., U.S. Pat. Nos. 4,957,773 and 4,603,044, the teachings of which are incorporated herein by reference). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. The liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposome's surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337–16342 (1990) and Leonetti, et al, *Proc. Natl. Acad. Sci.* (USA), 87:2448–2451 (1990). Other examples of antibody conjugation are disclosed in U.S. patent application Ser. No. 08/316,394, filed Sep. 30, 1994, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds. See, Heath, *Covalent Attachment of Proteins to Liposomes,* 149 *Methods in Enzymology* 111–119 (Academic Press, Inc. 1987). Other targeting methods include the biotin-avidin system.

In some cases, the diagnostic targeting of the liposome can subsequently be used to treat the targeted cell or tissue. For example, when a toxin is coupled to a targeted liposome, the toxin can then be effective in destroying the targeted cell, such as a neoplasmic cell.

The concentration of liposome compositions in the pharmaceutical formulations can vary widely, i.e., from less than about 0.05%, usually at or at least about 2–5%, to as much as 10 to 30% by weight, and will be selected primarily by fluid volumes, viscosities, etc., in accordance with the particular mode of administration selected. For diagnosis, the amount of composition administered will depend upon the particular label used (i.e., radiolabel, fluorescence label, and the like), the disease state being diagnosed and the judgment of the clinician, but will generally be between about 1 and about 5 mg per kg of body weight.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

VIII. EXAMPLES

A. Materials

All chemical reagents were of the high purity commercially available and were used without further purification. In order to quantify the polymer, PEAA was fluorescently labeled with a small amount of pyrene. The pyrene-labeled PEAA (Py-PEAA, Xn=200, MW=20 000) was obtained from Dr. D. A. Tirrell. EPC and MPB-DSPE were obtained from Northern lipids (Vancouver, BC, Canada). [$^3$H]cholesteryl hexadecyl ether was obtained from Du Pont (NEN Research Product). Cholesterol, dithiothreitol (DTT), Ellman's reagent [5,5'-dithiobis(2-nitrobenzoic acid)] (DTNB), calcein, 2-aminoethanethiol (AET), 4-pyrrolidinopyridine, decylamine and 1,3-dicyclohexylcarbodiimide (DCC) were obtained from Aldrich Chemical Corp. 1,2-dioleoyl-sn-glycero-3-phosphoethanolamine-N-(lissamine Rhodamine B sulfonyl) (Rh-PE) and 1,2-dioleoyl-sn-glycero-3-phosphoethanolamine-N-(7-nitro-1-1,3-benzoxadiazol-4-yl) (NBD-PE) were obtained from AVANTI Polar-Lipids, Inc. (Alabaster, Ala.).

Triethylamine, benzyl alcohol and trimethylsilyl iodide were purchased from Aldrich Chemical Co. and used without further purification. THF (Fisher, certified) was stirred over $CaH_2$, degassed, and distilled into a storage flask containing sodium/benzophenone. Fresh THF was obtained from this dark-purple solution by distillation into the reaction flask. 2-Ethylacrylic acid was synthesized by the procedure reported by Ferritto, M. S., and Tirrell, D. A., *Macromolecular Synthesis*, 11:59 (1992).

B. Methods

1. Preparation of Large Unilamellar Vesicles (LUV[calcein]s)

LUV[calcein]s can be prepared as described by Hope, et al., *Biochim. Biophys. Acta*, 812:55–65 (1985). Appropriate amounts of a lipid mixture containing a trace amount of a radiolabeled lipid marker ([$^3$H]-cholesterylhexadecyl ether, 1.33 $\mu$Ci/4 $\mu$mol) in chloroform were concentrated to a homogeneous lipid film under a stream of nitrogen gas and then dried in high vacuum overnight. The lipid film is then hydrated with 20 mM HBS, 100 mM NaCl and 100 mM calcein (pH 7.5) by vortex mixing. Subsequently, the solution is then frozen (liquid $N_2$) and thawed, and then extruded 10 times through two stacked 100 nm polycarbonate filters (Nuclepore) employing an extrusion device (Lipex Biomembranes, Inc. Vancouver, BC, Canada) at 55° C. Untrapped free calcein can be removed on a 1.1×20 cm Sepharose CL-6B column with HBS buffer (20 mM HBS, 100 mM NaCl, pH 7.5).

2. Coating of Lipo-PEAA onto LUV[calcein]s

Coating is one method of incorporating a Lipo-PEAA into a LUV. In this method, the LipoPEAA with 3% lipid (MW=20,000) is synthesized as described in Example 4 hereinbelow. The coating method can then be used for preparation of polymer-LUV[calcein] as described in detail in Example 5. Briefly, the Lipo-PEAA is dissolved in HBS and the pH of the solution is adjusted to about pH 7.4. An aliquot of the polymer solution with an appropriate amount of polymer is incubated with LUV[calcein]s overnight at room temperature. Uncoated free Lipo-PEAA was removed on a 1.1×20 cm Sepharose CL-6B column.

3. Calcein Release Assay

To minimize the pH effect on calcein fluorescence, the tested solutions were adjusted to between pH 6 and pH 7 before the fluorescence measurements. For the pH-dependent calcein release assay, the pH of the Lipo-PEAA-LUVs [calcein] was adjusted with 1% HCl solution; the solution was equilibrated for 10 minutes after each pH adjustment; 10 $\mu$l of aliquot were withdrawn and mixed with 1 mL of HBS (the large amount of buffer adjusted the pH of the solution back to pH 6.5–7.5), and the fluorescence intensity at 530 nm (excitation at 495 nm) was measured. For the time track of pH-dependent calcein release, the initial pH of 7.5 was maintained for a period of 10 to 15 minutes, after which the pH was adjusted to 5. At different times, an aliquot was withdrawn and mixed with HBS, and the fluorescence intensity of the solution was measured. The total fluorescence intensity of each sample was determined by addition of Triton X-100 (10% of lipid concentrations). The percent of calcein released was calculated as the following equation:

$$\% \text{ Release} = \frac{F_t - F_0}{F_f - F_0} \times 100$$

where $F_t$ is the fluorescence intensity after each pH adjustment, $F_0$ is the initial calcein fluorescence intensity, and Ff is the measurement of complete release by using detergent to solubilize the LUVs(calcein).

4. pH-Dependent Contents Leakage Assay

To determine whether the destabilization of a membrane-coated LipoPEAA is pH-dependent, a content release assay can be used. In this assay, a fluorescent marker, e.g., calcein, was encapsulated as an aqueous permeability marker. When a high concentration of calcein was encapsulated inside the vesicles, there was no, or very low fluorescence intensity due to calcein self-quenching. High fluorescence intensity is measured if calcein releases out of the vesicle and is diluted into solution.

5. Fusion Efficiency Measured by Lipid Mixing Assay

In order to assay the fusion efficiency of liposomes wherein a Lipo-PEAA is incorporated therein, the effect of an Lipo-PEAA on the stability of EPC/Chol (55:4570:30) LUVs, was studied. EPC is a naturally occurring mixture of phosphatidylcholine species bearing a variety of fatty acyl chains, and it consists predominantly of POPC. The addition of cholesterol to phospholipid bilayers decreases membrane permeability by affecting tighter packing lipids.

Fusion of PEAA-vesicles with artificial target membranes can be followed with a fluorescence resonance energy transfer assay (FRET) described by Struck, et al. (*Biochemistry*, 20:4093–4099 (1981)). In a typical experiment, LUVs are prepared containing the fluorescent lipids, N-(7-nitro-2-1,3-benzoxadiazol-4-yl)-dioleoylphosphatidyl-ethanolamine (NBD-PE) and N-(lissamine Rhodamine B sulfonyl)-dipalmitoylphosphatidyl-ethanolamine (Rh-PE) at 0.5 mol % and are coated with anchored-PEAA (PEAA-LUV[NBD/Rh]) as a Donor. Probe-free LUVs are prepared as acceptors. The Donor vesicles were mixed with probe-free LUV (Acceptor) in a 1 to 3 ratio (Donor/Acceptor). Upon fusion of a membrane labeled with the NBD-PE/Rh-PE pair, the two fluorophores diluted into the target membrane, resulting in a decrease of their overall surface density and a concomitant decrease of the RET efficiency. This decrease shows up as an increase of donor (NBD-PE) fluorescence. This assay can be used to assay pH-dependent fusion of PEAA-LUVs.

The initial pH of 7.5 of the solutions was maintained for 10–15 min, then the solutions were acidified to a pH less than about 5. At different times, an aliquot was withdrawn and the solutions were adjusted back to a pH 6.5–7.5. The fluorescence intensity of NBD-PE was then determined with an Aminco Bowman® Series 2 luminescence spectrometer at 530 nm under steady-state excitation at 495 nm. Any fusion of labeled LUV (Donor) with probe-free LUV results in increased distance between the NBD-PE and the Rh-PE, thereby decreasing RET efficiency. The total fluorescence intensity of each sample was determined by addition of Triton X-100 (10% of lipid concentrations). The percent of fusion (or lipid dilution) was calculated as:

$$\% \text{ Fusion} = \frac{F_t - F_0}{F_f - F_0}$$

where $F_t$ is the fluorescence intensity at each time point; $F_0$ is the initial fluorescence intensity, and $F_f$ is the measurement of complete dilution using detergent to solubilize the LUV.

Example 1

This example illustrates the use of the random point procedure to prepare Lipo-PEAA by EDC-mediated coupling reaction.

100 mg (100 mmol unit, unit MW=100) of Py-PEAA (polymer molecular weight, 20K, prepared as in example 4) and 3 mmol of 1-Decylamine [$CH_3(CH_2)_9NH_2$] were dissolved in 6 mL of water (pH 7.0). EDC (about 100 mg) was slowly added into the reaction mixture until the amine disappeared. The level of amine, during the reaction, was monitored by TLC ($CHCl_3$:MeOH:triethylamine=8:2:0.2, ninhydrin). The resultant derivative was precipitated by adjusting the pH of the solution from pH 2 to pH 3. The pellets were separated and redissolved in 2 M sodium hydroxide (NaOH) solution, stirred for 30 minutes, and pH was readjusted to pH 2 from pH 3. The suspension mixture was centrifuged, the pellets were separated and washed in water for 3 to 5 times and lyophilized. The yield reached up to 85%.

Example 2

This example illustrates a method for preparing N-terminal-linked Lipo-PEAA by anionic the polymerization reaction. The schematic of the reaction is outlined in FIG. 2.

A. 1,1-Diphenylpropyllithium

An oven-dried 50 mL round-bottomed flask with a glass stopcock on the side-arm was equipped with a magnetic stirring bar and capped with a rubber septum. The flask was purged three times with purified argon and evacuated each time. Finally it was filled with argon and closed with the glass stopcock. Tetrahydrofuran (THF) 10 mL (Fisher, certified) was stirred over $CaH_2$, degassed, and distilled into a storage flask containing sodium/benzophenone. Fresh THF obtained from this dark-purple solution by distillation and 1,1-diphenylethylene (0.53 mL, 3.0 mmol, 1,1-diphenylethylene (97%, Aldrich Chemical Co.) was stirred over a few chips of potassium metal in a flask for one day at 75° C. in a silicon oil bath with intermittent degassing. A dark blue color developed, indicating the formation of the radical anion from the reaction of the potassium metal with some impurities, e.g., benzophenone. The middle boiling fraction was distilled at 80–82° C. into a storage flask and stored in the refrigerator) were first added to the flask by syringe and stirred for ten minutes at room temperature. Methyllithium (2.1 mL, 3.0 mmol (Methyllithium 1.4 M solution in diethyl ether), Aldrich Chemical Co., used without purification) was then introduced slowly by syringe. The solution turned dark red indicating the formation of 1,1-diphenylpropyllithium. It was further stirred for 2 hours before polymerization.

B. Poly(t-butyl Methacrylate)-block-poly(benzyl 2-ethylacrylate)

An oven-dried 100 mL reaction flask fitted with a CHEM-CAP™ valve (reaction flask, airfree, with CHEM-CAP™ valve was obtained from Chemglass, Inc.) and magnetic stirring bar was connected to a high vacuum line. It was purged three times with purified argon and evacuated each time. About 20 mL of THF (Fisher, certified) was stirred over $CaH_2$, degassed, and distilled into storage flask containing sodium/benzophenone. Fresh THF was distilled from the dark-purple solution in storage container directly into a reactor that was cooled to −78° C. by dry ice/isopropanol bath. The reactor was filled with argon and the 1,1-diphenylpropyllithium initiator solution (1 mL of 0.3 M stock solution, 0.3 mmol) was added by syringe. The reactor contents were stirred continuously with a magnetic stirrer and temperature was maintained at −78° C. The color of the initiator remained dark purple until the addition of monomer. t-Butyl methacrylate (0.44 g, 3.1 mmol) (tBMA) monomer was first introduced slowly over a 1–2 minute period and the initiator color immediately changed to pale yellow. 15 minutes after the addition of tBMA, benzyl 2-ethylacrylate (BzEA) (8 g, 42.1 mmol) were added all at once and reaction was allowed to proceed to completion for 15 hours. The polymerization mixture was stopped by adding 2 mL of methanol, stirred for 20 minutes and then poured into 300 mL of methanol. The polymer was separated by filtration and redissolved in 20 mL of THF and precipitated into 300 mL of methanol. Drying in a vacuum oven at 30° C. for 24 hours yielded poly(t-butyl methacrylate)-block-poly(benzyl 2-ethyl acrylate) (8.2 g, 98%).

C. Poly(methacrylic acid)-block-Poly(Benzyl 2-ethylacrylate)

3 g of poly(t-butyl methacrylate)-block-poly(benzyl 2-ethylacrylate) was dissolved in a mixture of 100 mL of 1,4-dioxane and 20 mL of 10% hydrochloric acid. The solution was heated at reflux for 12 hours then cooled to room temperature. After the solvents were partially evaporated using rotavap, the product was diluted with 10 mL THF and then slowly poured into 300 mL of methanol. The polymers precipitated were isolated by filtration and dried under vacuum at room temperature. The final yield was 2.5 g (86%).

D. Poly(methacrylic acid-co-hexadecyl acrylamide)-block-poly(benzyl 2-ethylacrylate)

A 100 mL single-neck, round-bottomed flask fitted with a reflux condenser, and magnetic stirring bar was charged with poly(methacrylic acid)-block-poly(benzyl 2-ethylacrylate) (2 g, 0.7 meq. methacrylic acid), hexadecylamine (1.7 g, 7 mmol tech. 90% Aldrich Chemical Co. recrystallized from benzene and dried under vacuum) and 20 mL of benzene. After stirring at 70° C. for 2 hours, 1,3-dicyclohexylcarbodiimide (0.43 g, 2.1 mmol) in 10 mL of benzene was added to the reaction flask. The initially clear solution became turbid, and insoluble 1,3-dicyclohexylurea was precipitated within an hour. The reaction was continued for 24 hours at 70° C. The insoluble urea was filtered and the filtrate was poured into 300 mL of methanol to precipitate the polymer. It was redissolved in 10 mL THF and precipitated into 300 mL of methanol at least 3 times to completely remove the hexadecylamine. The isolated polymers were filtered and dried under vacuum at 30° C. Final yield 1.5 g (72%).

E. Poly(methacrylic acid-co-hexadecyl acrylamide)-block-poly(benzyl 2-ethylacrylic acid)

To a solution of poly(methacrylic acid-co-hexadecyl acrylamide)-block-poly(benzyl 2-ethylacrylate) (1 g, 4.7 meq. BzEA) in 20 mL of chloroform was added trimethylsilyliodide (1.7 mL, 12 mmol, iodotrimethylsilane, 97%, Aldrich Chemical Co., was, used without purification) by syringe under argon. The reaction mixture was stirred for 48 hours at room temperature and then warmed to 60° C. for 3 hours. The dark-red colored reaction mixture was cooled to room temperature and transferred to a separatory funnel. It was washed with 100 mL of water and 100 mL of 5% aqueous sodium bisulfite to remove residual iodide. Polymers suspended between the chloroform and water layers were filtered and washed with 100 mL of water treated with 10 mL of 1 N sodium hydroxide for 3 hours at 80° C. to cleave the anhydride rings that formed during debenzylation. The infrared band at 1795 and 1750 in the intermediate polymer disappeared. Finally the basic solution was slowly poured into 200 mL of 1 N hydrochloric acid to precipitate the polymer. The polymer was separated by filtration, redissolved in 5 mL of methanol and precipitated in 100 mL of ether. Drying under vacuum at room temperature yielded poly(methacrylic acid-co-hexadecyl acrylamide)-block-poly (2-ethylacrylic acid) (0.3 g, 55%).

Example 3

Figure 3:
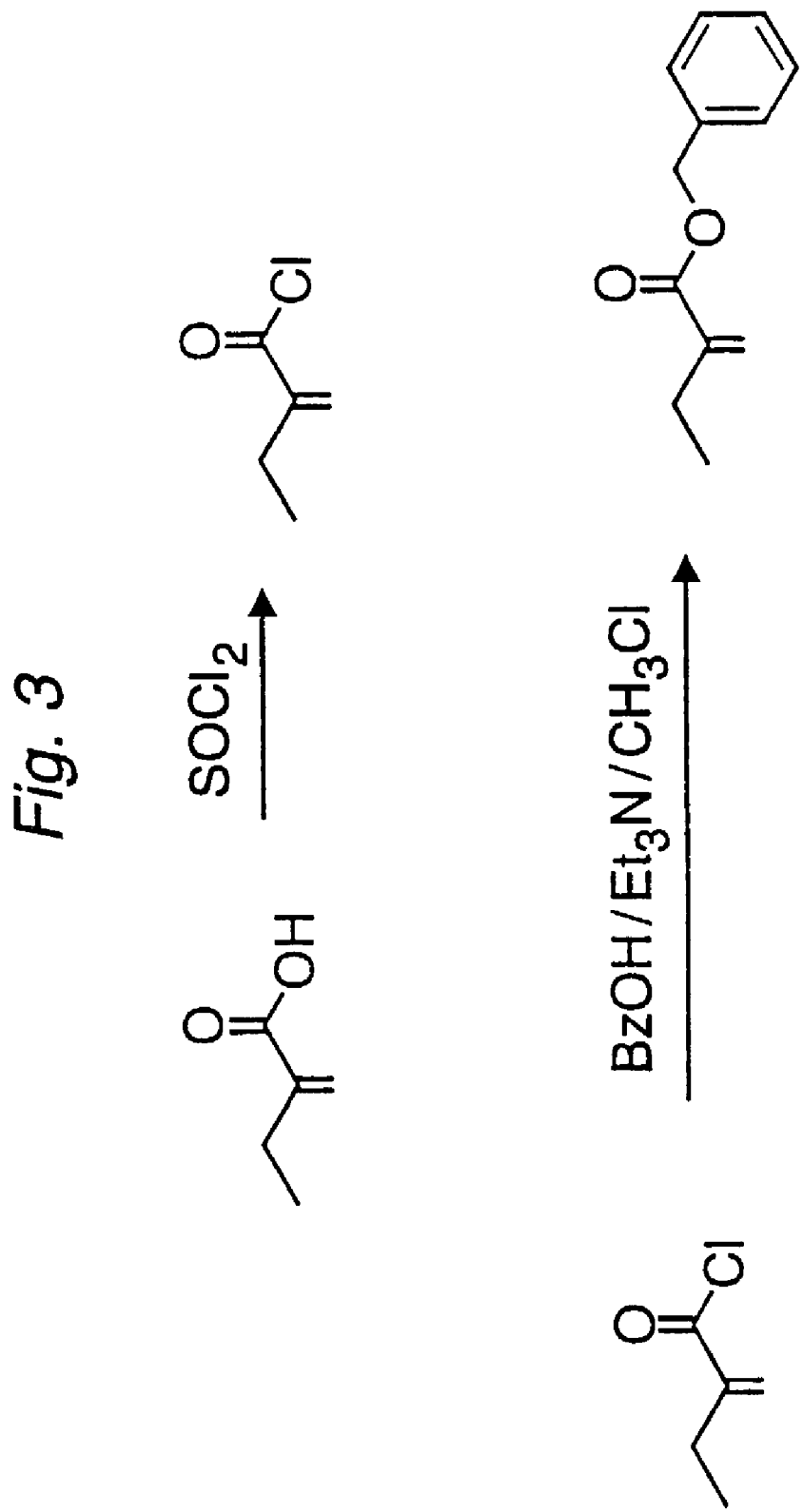
FIG. 3 illustrates the synthesis of Benzyl 2-ethylacrylate (BzEA).

This example illustrates a method of synthesis of Benzyl 2-ethylacrylate (BzEA). The schematic of the reaction is illustrated in FIG. 3.

A. 2-ethylacryloyl chloride.

Thionyl chloride (108 g, 0.9 mol, Thionyl chloride, 99+% Aldrich Chemical Co., used without purification) was placed in a 500 mL double-necked round-bottomed flask equipped with a magnetic stirring bar, a reflux condenser and a dropping funnel. The condenser and funnel were fitted with calcium chloride guard-tubes. 2-ethylacrylic acid (75 g, 0.75 mol, 2-ethylacrylic acid prepared according to the procedure published by Ferritto and Tirrell and used without purification) was placed in the dropping funnel and dripped slowly into the flask. Sulphur dioxide evolved and the liquid darkened considerably. When all of the 2-ethylacrylic acid had been added, the mixture was refluxed for 2 hours. The apparatus was rearranged for distillation and 2-ethylacryloyl chloride boiling at 105–107° C./760 mmHg was collected (78 g, 88%).

B. Benzyl 2-ethylacrylate.

A mixture of benzoyl alcohol (27 g, 0.25 mol, benzyl alcohol, 99+% A.C.S. reagent, Aldrich Chemical Co., used without purification) and triethylamine (16 g, 0.16 mol, triethylamine, 99%, Aldrich Chemical Co., used without purification) was placed in the a double-necked, round-bottom flask equipped with a reflux condenser and thermometer. The contents were stirred with a magnetic stirring bar and the temperature was lowered to 0° C. A solution of 2-ethylacryloyl chloride (8 g, 0.07 mol) in 20 mL chloroform was slowly added to the reaction flask. The reaction was strongly exothermic, and the rate of dropping was regulated so that temperature of mixing did not exceed 30° C. After the addition was complete, the mixture was heated under reflux for 4 hours. After the reaction mixture was cooled, 40 mL of ice-cold 6 N sulfuric acid was stirred in and the product was extracted with three 150 mL portions of hexane. The combined hexane extracts were washed once with 6 N sulfuric acid, twice with water, twice with 10% potassium carbonate, once with saturated sodium chloride, twice with ethanol/water (50/50) mixture and finally dried over anhydrous magnesium sulfate. The hexane was evaporated and the yellow residue was fractionally distilled (bp 66–68° C./1 mmHg) to yield pure colorless benzyl 2-ethylacrylate (10 g, 75%).

Example 4

This example illustrates a method for fluorescently labeling PEAA for quantification purposes.

Figure 4:
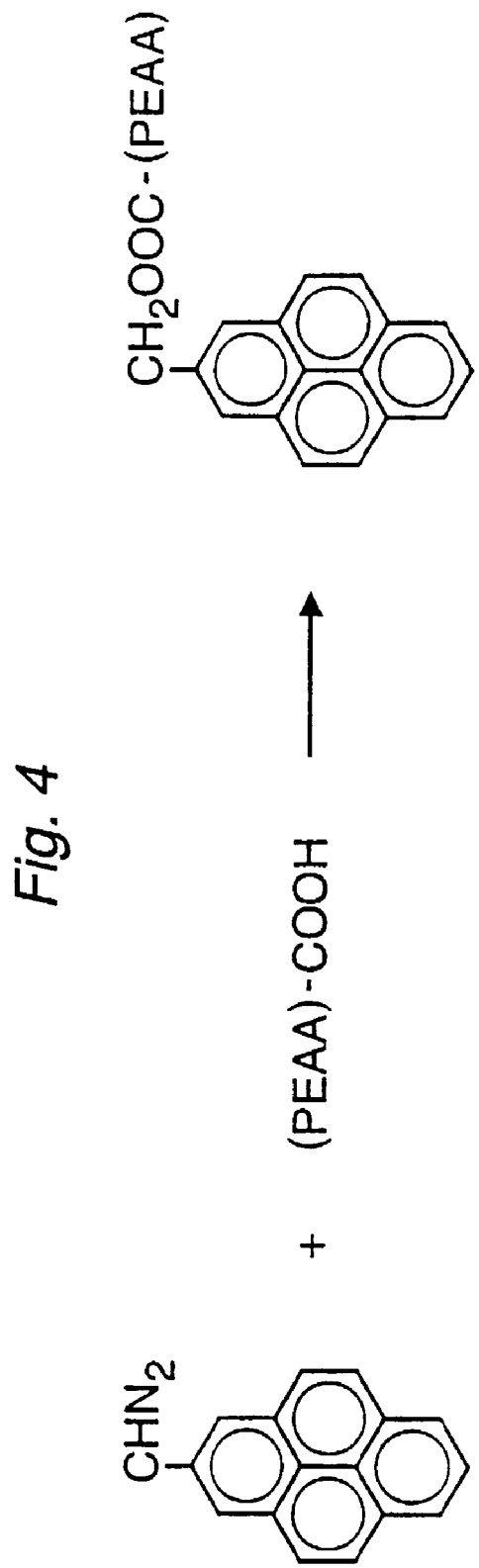
FIG. 4 illustrates the chemical reaction of PEAA with Pyrenol Diazomethane (PDAM) to form pyrene-PEAA which allows for the quantification of the polymer.

PEAA was fluorescently-labeled using 1-pyrenyldiazomethane (PDAM) with a small amount of carboxylic group of PEAA as shown in FIG. 4.

50 mg of PEAA (FW: 20,000) was dissolved in 5 mL methanol, followed by the addition of 6 mg PDAM (in 0.5 mL Chloroform). The reaction mixture was stirred for 18 hours. Then, 0.5 mL of 2 M acetic acid (in methanol) was added and stirred for 2 hours. The product was purified by precipitation in methanol/diethyl ether (1:20) several times. The yield reached 70%. The UV absorbance showed that the modification of PEAA with pyrene was 0.5 per mol PEAA. The pH-sensitivity was not significantly altered by fluorescent labeling. Pyrene-labeled PEAA can be quantified by measuring pyrene fluorescence on an Aminco Bowman fluorometer at 396 nm (excitation at 344 nm), emission 396 nm.

Example 5

This example illustrates a method of incorporating Lipo-PEAA into LUV liposomes using the coating method.

Figure 5:
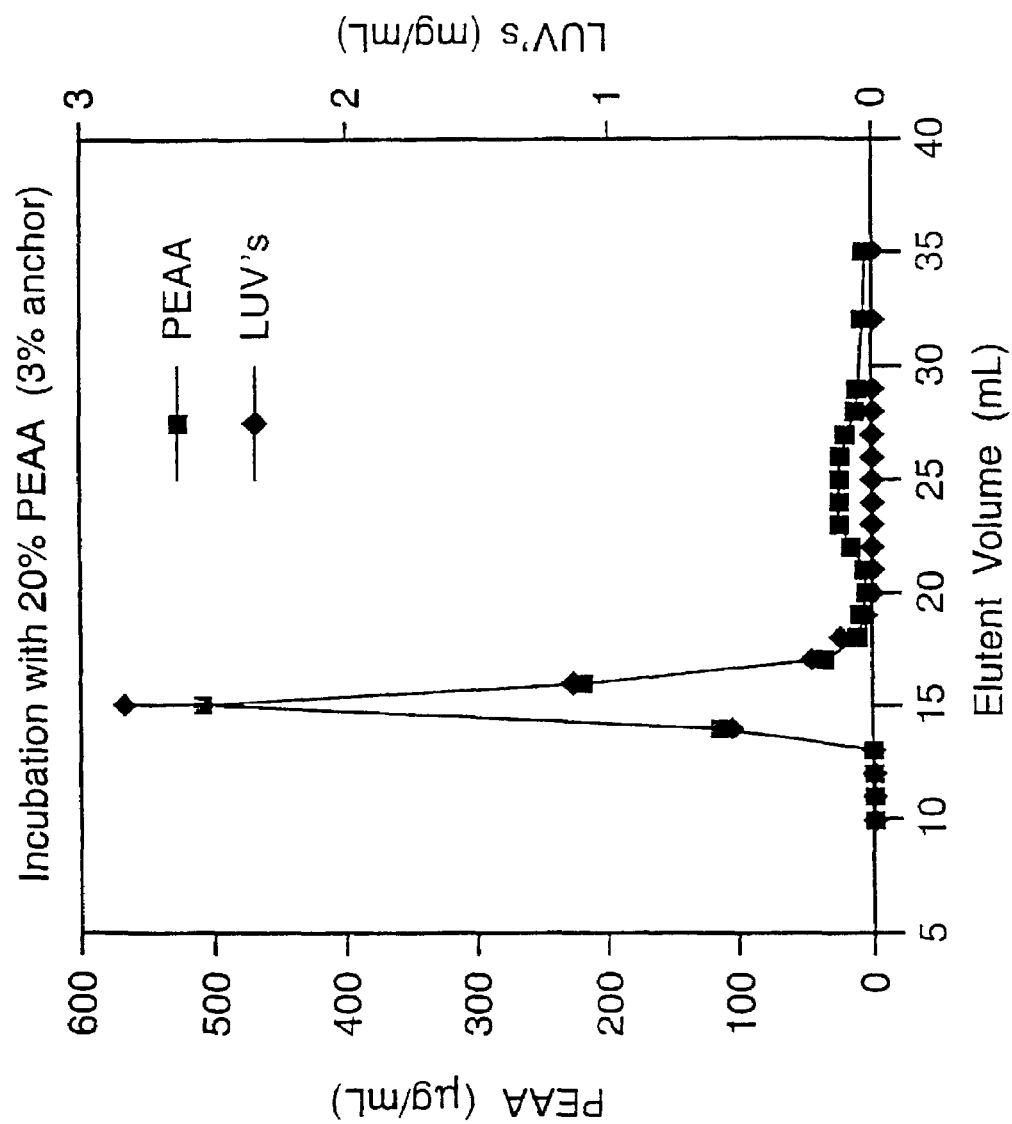
FIG. 5 illustrates the elution profile for separating lipids and PEAA.
Figure 6:
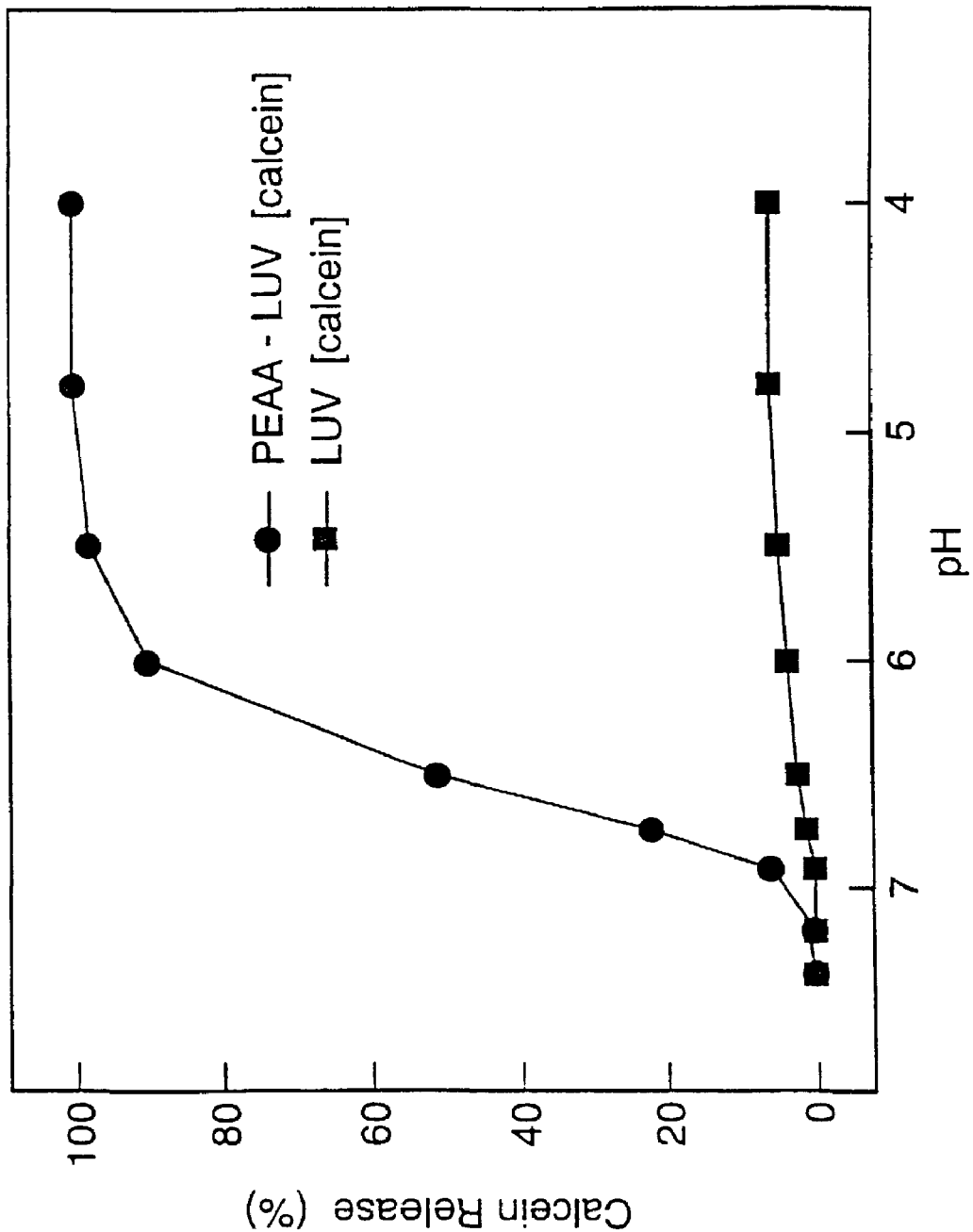
FIG. 6 illustrates the pH-dependent calcein release of PEAA-lipid particle(calcein).
Figure 7:
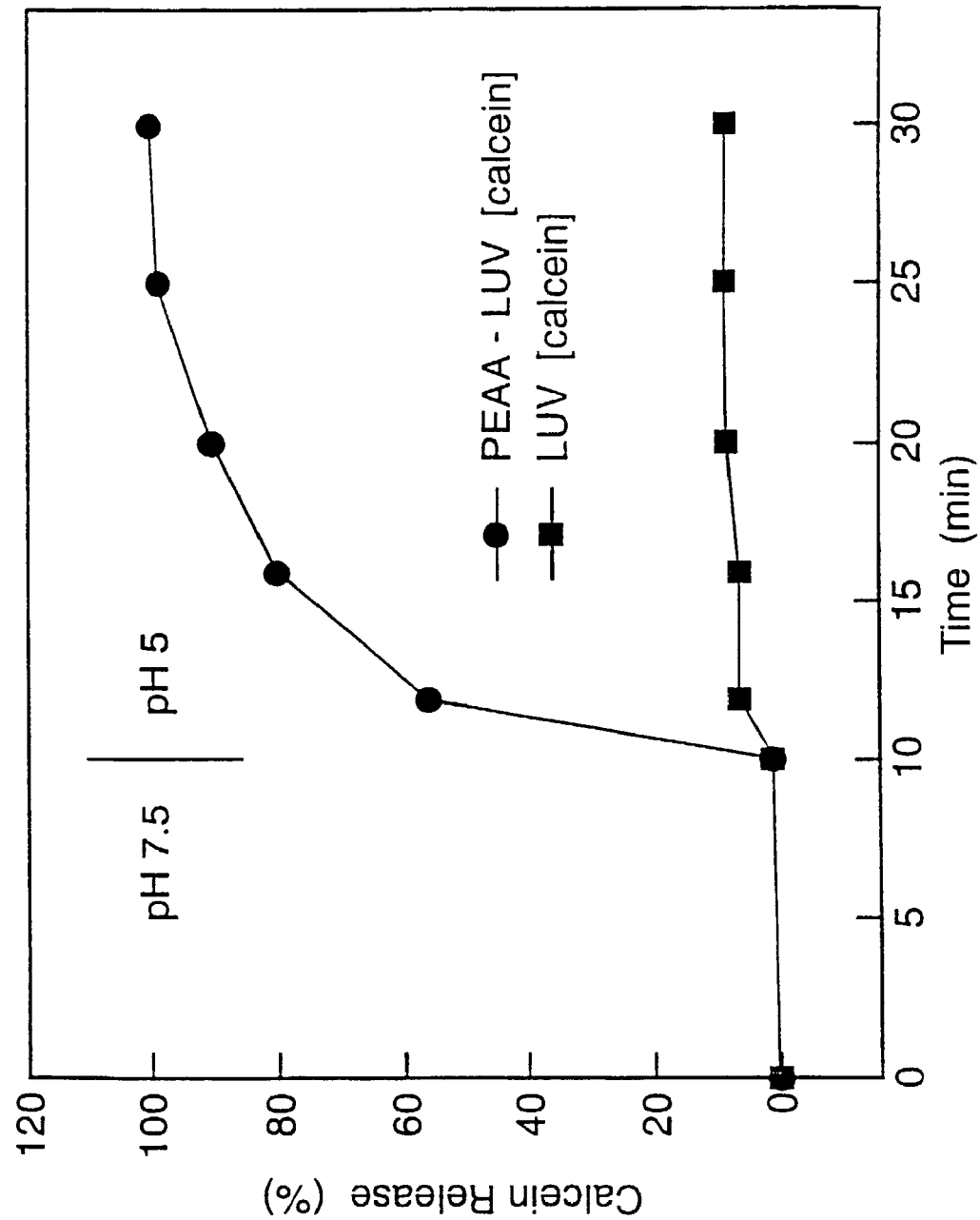
FIG. 7 illustrates the time course of pH-dependent calcein release of PEAA-lipid particle(calcein)s.
Figure 8:
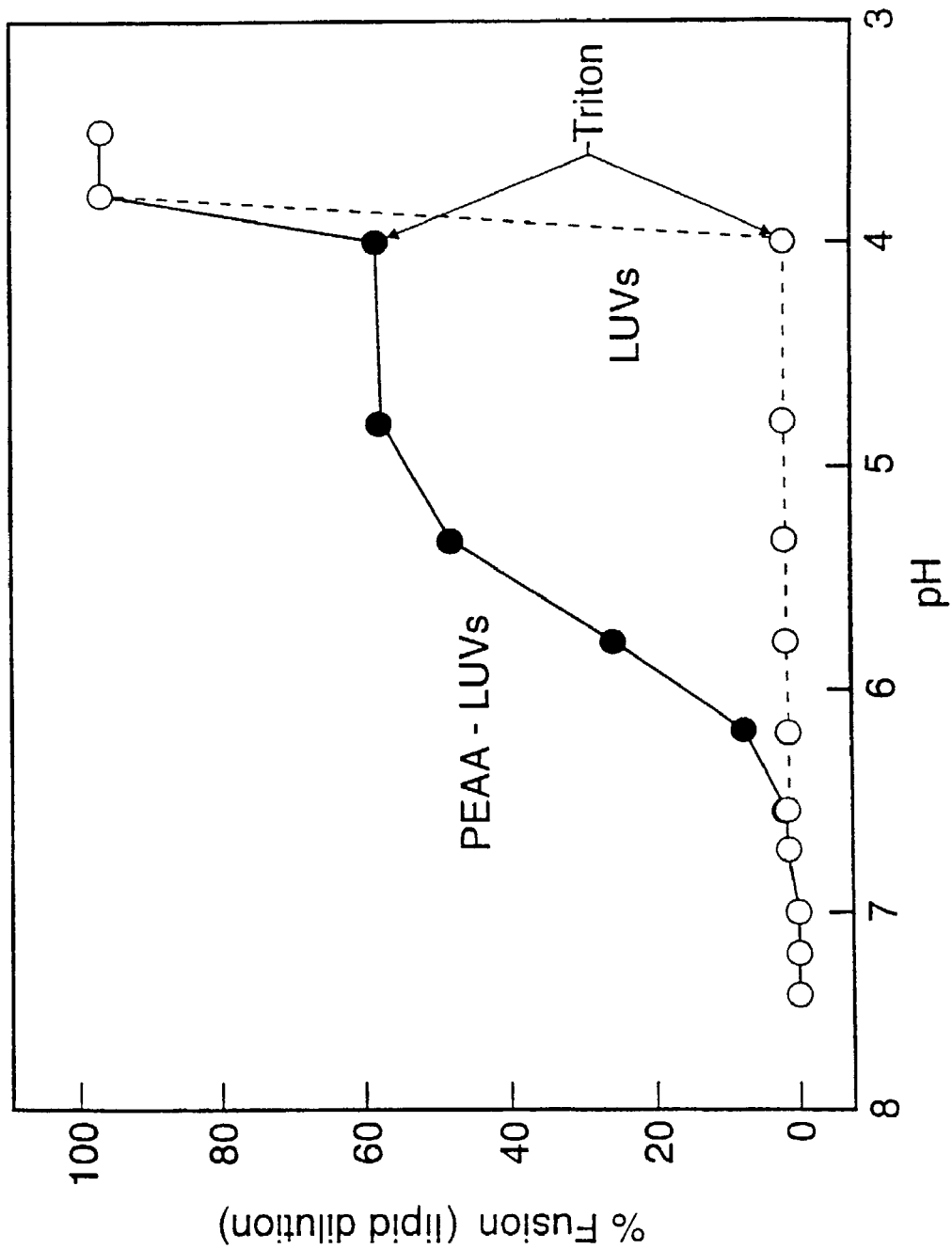
FIG. 8 illustrates the pH-dependent fusion of PEAA-lipid particles.
Figure 9:
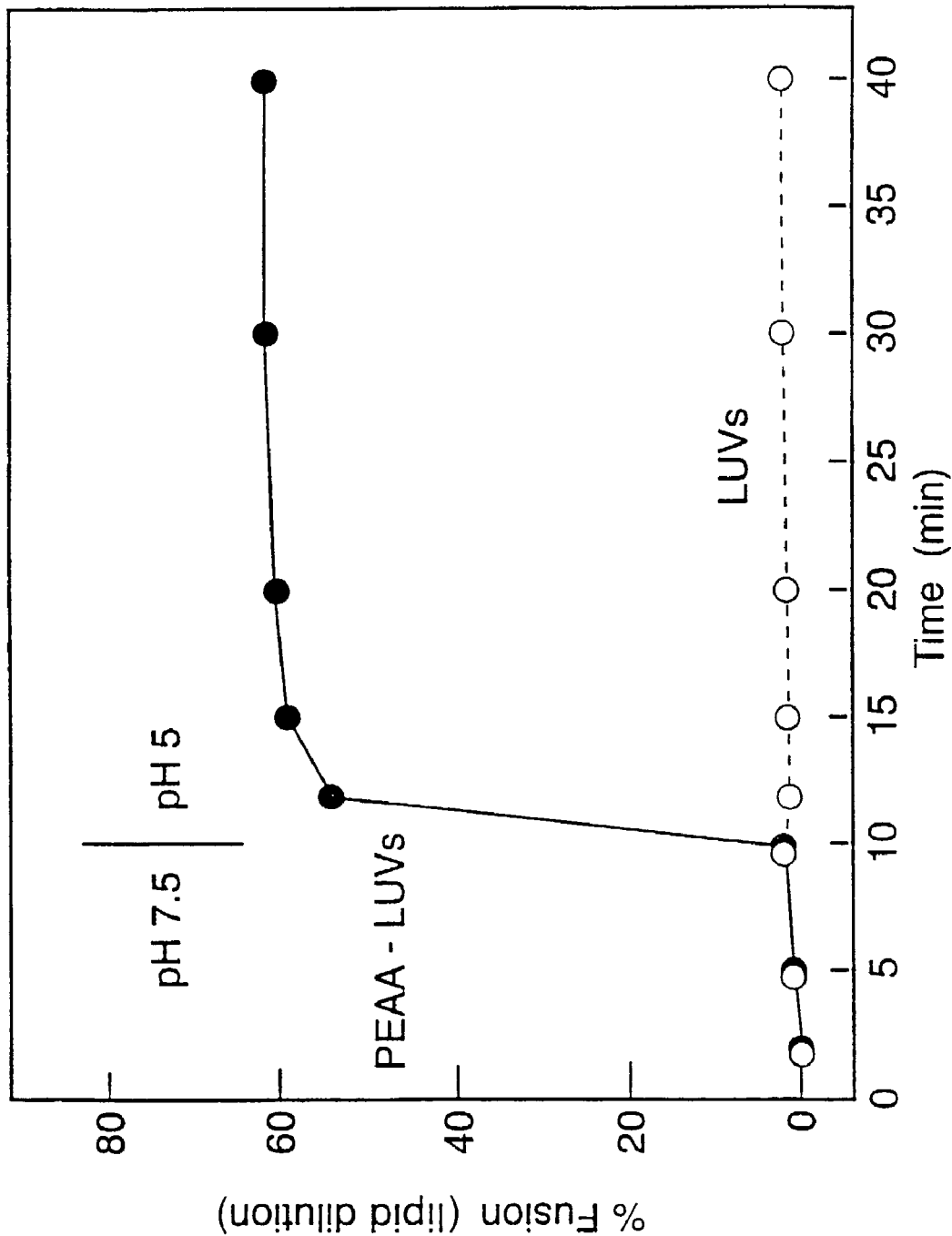
FIG. 9 illustrates the time course of pH-dependent fusion of PEAA-lipid particles.
Figure 10A:
FIG. 10 illustrates the intracellular calcein release of PEAA-lipid particle(calcein)s synthesized by the random point method.
Figure 10B:
Figure 10C:
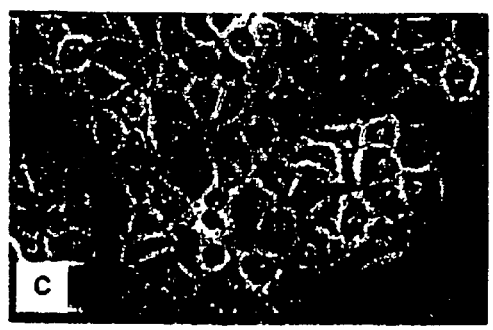
Figure 10D:
Figure 11:
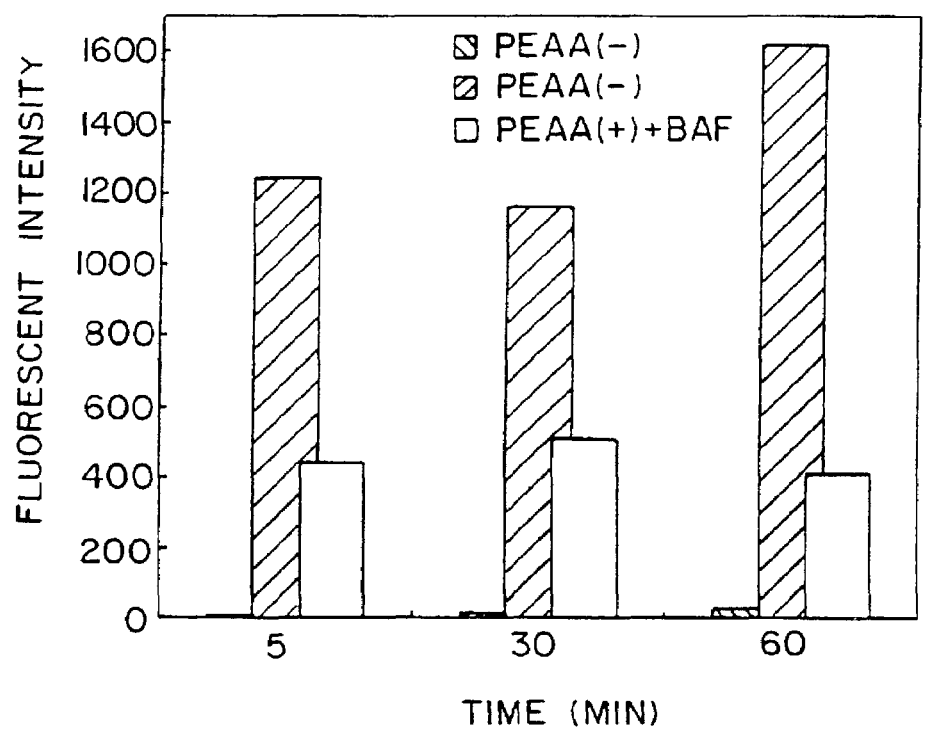
FIG. 11 illustrates the intracellular calcein release and inhibition study of PEAA-lipid particle(calcein)s synthesized by the random point method.
Figure 12A:
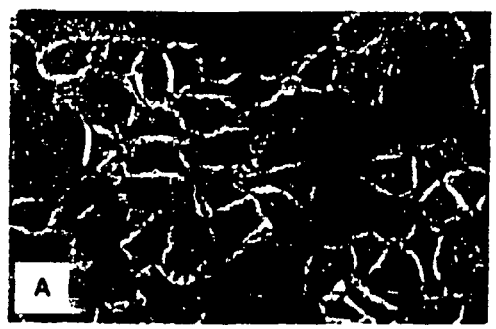
FIG. 12 illustrates the intracellular calcein release of PEAA-lipid particle(calcein)s synthesized by the anionic polymerization method.
Figure 12B:

1.2 mg of Lipo-PEAA (3% modified decyl-PEAA) was incorporated with 6.0 mg of LUVs (EPC/Chol, 60:40) in 1.0 mL HBS buffer (pH 7.5) at room temperature and left to stand 16 hours. The mixture was eluted on a Sepharose CL-6B column (1.5×20 cm) and the fractions were assessed for lipids and polymers. Any uncoated polymer will separate from polymer-TCS on a Sepharose CL-6B column as shown in FIG. 5. The polymer coating is irreversible. No free polymers were detected when the mixture containing polymer-TCS was eluted in HBS and separated on a Sepharose CL-6B column.

Example 6

This example illustrates a method of incorporating calcein in a LUV formulated with a Lipo-PEAA.

LUV[calcein]s were prepared as described by Hope, et al., *Biochim. Biophys. Acta,* 812:55–65 (1985). Appropriate amounts of lipid mixture containing a trace amount of a radiolabeled lipid marker ([3H]-cholesterylhexadecyl ether, 1.33 $\mu$Ci/4 $\mu$mol) in chloroform were concentrated to a homogeneous lipid film under a stream of nitrogen gas and then dried in a high vacuum overnight. The lipid film was hydrated with 20 mM HBS, 100 mM NaCl and 100 mM calcein (pH 7.5) by vortex mixing. Subsequently, the solutions were frozen (liquid N2) and thawed, and then extruded 10 times through two stacked 100 nm polycarbonate filters (Nucleopore) using an extrusion device (Lipex Biomembranes, Inc. Vancouver, BC, Canada) at 55° C. Untrapped free calcein was removed on a 1.1×20 cm Sepharose CL-6B column with HBS buffer (20 mM HBS, 100 mM NaCl, pH 7.5).

The Lipo-PEAA with 3% lipid (MW 20K) was dissolved in HBS and the pH of the solution was adjusted to pH 7.4. An aliquot of polymer solution with an appropriate amount of polymer with LUV[calcein]s was incubated overnight at room temperature. Uncoated, free Lipo-PEAA was removed on a 1.1×20 cm Sepharose CL-6B column.

Example 7

This example illustrates the assay used to evaluate the pH-dependent characteristic of a LUV formulated with PEAA by measuring the amount of calcein released.

To minimize the pH effect on calcein fluorescence, the tested solution was adjusted to between pH 6 and pH 7 before the fluorescence measurements. For the pH-dependent calcein release assay, the pH of the polymer-LUVs [calcein] was adjusted with 1% HCl solution. The solution was equilibrated for 10 minutes after each pH adjustment. A 10 $\mu$l aliquot was taken and mixed with 1 mL of HBS (the large amount of buffer was adjusted to between pH 6.5 and 7.5), and the fluorescence intensity was measured at 530 mm (excitation at 495 nm).

To evaluate pH-dependent calcein release over time, the initial pH 7.5 was maintained for a period of 10 to 15 minutes, after which the pH was adjusted to pH 5. At different intervals, an aliquot was withdrawn, mixed with HBS, and the fluorescence intensity measured. The total fluorescence intensity of each sample was determined by addition of Triton X-100 (10% of lipid concentrations). The percentage amount of calcein released was calculated as follows:

$$\% \text{ Release} = \frac{F_t - F_0}{F_f - F_0} \times 100$$

where $F_t$ is the fluorescence intensity after each pH adjustment, $F_0$ is the initial calcein fluorescence intensity, and $F_f$ is the measurement of complete calcein released after detergent solubilization of the LUVs(calcein).

Example 8

This example illustrates a method of evaluating proton-induced fusion of a LUV formulated with a PEAA using a lipid mixing assay.

Fusion of lipid particles was monitored by fluorescence resonance energy transfer (RET) assay between the headgroup labeled probes NBD-PE and Rh-PE as described by Struck, et al. (*Biochemistry,* 20:4093–4099 (1981)). Typically, both probes (0.5 mol % of NBD-PE and Rh-PE) were incorporated into the same liposome vesicles, and the probe-labeled LUVs were then used for polymer coating. The polymer coated LUVs[NBD/Rh] (PEAA-LUV[NBD/Rh] were used as a Donor in the lipid mixing assay. The Donor vesicles were mixed in different ratios with probe-free LUV (Acceptor). The solutions were maintained at their initial pH of 7.5 for a period of 10 to 15 minutes, and then acidified to pH<5. At different times, aliquots were withdrawn, adjusted back to between pH 6.5 and pH 7.5, and the fluorescence intensity of NBD-PE was determined by Aminco Bowman® Series 2 luminescence spectrometer at 530 nm under steady-state excitation at 495 nm. Any fusion of labeled LUV (Donor) with probe-free LUV will result in increased distance between the NBD-PE and Rh-PE, thereby decreasing RET efficiency. The total fluorescence intensity of each sample was determined by addition of Triton X-100 (10% of lipid concentrations). The percent of fusion (or lipid dilution) was calculated as $$\% \text{ Fusion} = \frac{F_t - F_0}{F_f - F_0}$$

where $F_t$ is the fluorescence intensity at each time points; $F_0$ is the initial fluorescence intensity, and $F_f$ is the measurement of complete dilution by using detergent to solubilize the LUVs.

Example 9

This example illustrates a method for evaluating calcein release in cultured cells.

COS-7 cells, an African monkey kidney cell line was cultured in DMEM supplemented with 10% FBS in a humidifier incubator (5% $CO_2$) at 37° C.

$10^4$ COS-7 cells were plated in a 24-well culture plate containing 1 mL of DMEM-10% FBS 24 hours prior to the experiment. Cells were washed three times with PBS-CM buffer and then incubated with liposomes containing 200 mM calcein (with or without PEAA) at 1 mM lipid for the desired periods. After incubation, cells were washed five times with PBS-CM buffer and viewed with a microscope equipped with phase contrast and epifluorescence with an excitation filter set that produces excitation in the 470–500 nm range. The attachment of the filter allows observation of fluorescence emission in the 515 to 540 nm range with a long wave pass dichroic mirror and barrier filter.

Liposomes containing Rd-PE were prepared using EPC/Chol/Rd-PE (59:40:1, mol/mol/mol) as the membrane lipids. Cells were plated in 12 wells containing 2 mL of DMEM-10% FBS 24 hours prior to the experiment. Cells were washed 3 times with PBS-CM and then incubated with the liposomes (1.0 mM) dispersed in PBS-CM at 37° C. for desired periods.

After incubation, the cells were washed five times with PBS-CM and dislodged by treatment with tripsome for 5 minutes. Fluorescencent intensity of Rd-PE associated with cells at 525 nm were measured at an excitation wavelength of 450 nm. For calibration, the fluorescencent intensities for the liposome suspensions alone were also measured. The amount of liposomes associated with a cell was estimated from the calibration curve. The cell number was determined by estimating cell protein concentration by the Lowry assay.

All publications and other references or patents cited or listed herein are incorporated by reference. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of the formula

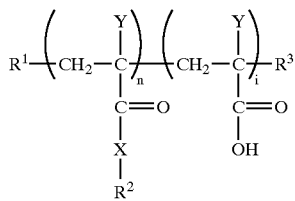

wherein:
- $R^1$ is a member selected from the group consisting of hydrogen, hydroxyl, amino, optionally-substituted alkyl and a ligand;
- Y is a member selected from the group consisting of hydrogen, optionally-substituted alkyl, optionally-substituted cycloalkyl, optionally-substituted aryl and optionally-substituted heteroaryl;
- X is a member selected from the group consisting of optionally-substituted amino, oxygen, sulfur and a carbon single bond;
- $R_2$ is a member selected from the group consisting of $C_6$–$C_{26}$ alkyl, $C_6$–$C_{26}$ alkenyl, dialkylglycerolyl, dialkenylglycerolyl, diacylglycerolyl, 1,2-diacyl-sn-glycero-3-phosphoethylenyl, 1,2-dialkoxy-3-aminopropanyl and 1,2-diacyloxy-3-aminopropanyl;
- R3 is a member selected from the group consisting of hydrogen, hydroxyl, amino, optionally-substituted alkyl and a ligand;
- n is greater than 1; and
- i is greater than 1.

2. A compound in accordance with claim 1, wherein:
- Y is a member selected from the group consisting of hydrogen, optionally-substituted $C_1$–$C_4$ alkyl, optionally-substituted $C_5$–$C_6$ cycloalkyl and optionally-substituted phenyl;
- X is a member selected from the group consisting of optionally-substituted amino, oxygen and sulfur;
- $R^2$ is a member selected from the group consisting of $C_6$–$C_{26}$ alkyl and $C_6$–$C_{26}$ alkenyl;
- n and i, added together, have a sum of 40 to 250.

3. A compound in accordance with claim 1, wherein:
- Y is a member selected from the group consisting of hydrogen, optionally substituted C1–C4 alkyl, optionally substituted C5–C6 cycloalkyl and optionally substituted phenyl;
- X is optionally-substituted amino;
- $R^2$ is a member selected from the group consisting of $C_6$–$C_{26}$ alkyl and $C_6$–$C_{26}$ alkenyl;
- n and i added together have a sum of 40 to 250.

4. A compound in accordance with claim 1, wherein:
- Y is a member selected from the group consisting of hydrogen, optionally substituted C1–C4 alkyl, optionally-substituted C5–C6 cycloalkyl and optionally substituted phenyl;
- X is a carbon single bond;
- $R^2$ is a member selected from the group consisting of dialkylglycerolyl, dialkenylglycerolyl, diacylglycerolyl, 1,2-diacyl-sn-glycero-3-phosphoethylenyl and 1,2-dialkoxy-3-aminopropanyl and 1,2-diacyloxy-3-aminopropanyl;
- n and i added together have a sum of 40 to 250.

5. A compound in accordance with claim 1, wherein:
- Y is a member selected from the group consisting of hydrogen, optionally substituted $C_1$–$C_4$ alkyl, optionally-substituted C5–C6 cycloalkyl and optionally-substituted phenyl;
- X is a carbon single bond;
- $R^2$ is a member selected from the group consisting of dialkylglycerolyl, dialkenylglycerolyl, diacylglycerolyl, 1,2-dialkoxy-3-aminopropanyl and 1,2-diacyloxy3-aminopropanyl; and
- n and i, added together, have a sum of 40 to 250.

6. A compound in accordance with claim 1, wherein:
- $R^3$ is a ligand, said ligand being a member selected from the group consisting of a lipid, polyethylene glycol and a compound of the formula

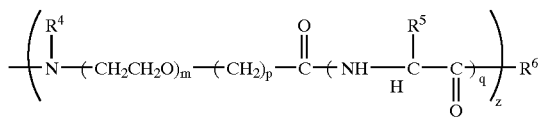

wherein:
- $R^4$ is a member selected from the group consisting of hydrogen and alkyl;
- R is a member of the group selected from hydrogen, optionally substituted alkyl, optionally-substituted aryl and a side chain of an amino acid;
- $R^6$ is a member selected from the group consisting of hydrogen, halogen, hydroxy, alkoxy, mercapto, hydrazino, amino and $NR^7R^8$, wherein $R^7$ and $R^8$ are independently hydrogen or alkyl;
- z is 4 to 80; m is 2 to 6;
- p is 1 to 4; and q is 0 or 1.

7. A compound in accordance with claim 1, wherein:
- R is a member selected from the group consisting of $C_{10}$–$C_{18}$ alkyl and $C_{10}$–$C_{18}$ alkenyl.

8. A compound in accordance with claim 1, wherein:
- $R^2$ is a member selected from the group consisting of dialkylglycerolyl and dialkenylglycerolyl, wherein said dialkyl groups are $C_{10}$–$C_{18}$ dialkyl and said dialkenyl groups are $C_{10}$–$C_{18}$ dialkenyl.

9. A compound in accordance with claim 1, wherein:
- $R^2$ is a member selected from the group consisting of diacylglycerolyl and 1,2-diacyl-sn-glycero-3-phosphoethylenyl, wherein said diacyl groups are $C_{10}$–$C_{18}$ diacyl.

10. A compound in accordance with claim 1, wherein:
- $R^2$ is a member selected from the group consisting of $C_{10}$ alkyl and $C_{10}$ alkenyl.

11. A compound in with claim 1, wherein:
R² is a member selected from the group consisting of dialkylglycerolyl and dialkenylglycerolyl, wherein said dialkyl groups are $C_{10}$ dialkyl and said dialkenyl groups are $C_{10}$ dialkenyl.

12. A compound in accordance with claim 1, wherein:
R² is a member selected from the group consisting of diacylglycerolyl and 1,2-diacyl-sn-glycero-3-phosphoethylenyl, wherein said diacyl groups are $C_{10}$ acyl.

13. A pH-sensitive liposome, said liposome comprising a lipid and a compound of the formula

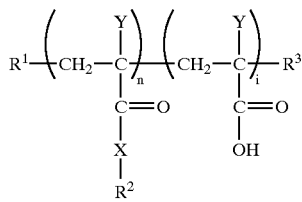

wherein:
R¹ is a member selected from the group consisting of hydrogen, hydroxyl, amino, optionally-substituted alkyl and a ligand;
Y is a member selected from the group consisting of hydrogen, optionally substituted alkyl, optionally-substituted cycloalkyl, optionally-substituted aryl and optionally-substituted heteroaryl;
X is a member selected from the group consisting of optionally-substituted amino, oxygen, sulfur a carbon single bond;
R₂ is a member selected from the group consisting of $C_6$–$C_{26}$ alkyl, $C_6$–$C_{26}$ alkenyl, dialkylglycerolyl, dialkenylglycerolyl, diacylglycerolyl, 1,2-diacyl-sn-glycero-3-phosphoethylenyl, 1,2-dialkoxy-3-aminopropanyl and 1,2-diacyloxy-3-aminopropanyl;
R3 is a member selected from the group consisting of hydrogen, hydroxyl, amino, optionally-substituted alkyl and a ligand;
n is greater than 1; and
i is greater than 1.

14. A pH-sensitive liposome in accordance with claim 13 wherein said liposome is fusogenic.

15. A pH-sensitive liposome in accordance with claim 13 wherein said lipid is a member selected from the group consisting of phosphoglycerides, sphingolipids, phosphatidylcholine, phosphatidylethanolamine, lipolyamines, and cholesterol-based lipids.

16. A pH-sensitive liposome in accordance with claim 15 wherein said lipid is a phosphatidylcholine.

17. A pH-sensitive liposome in accordance with claim 16 wherein said phosphatidylcholine lipid is a member selected from the group consisting of distearoylphosphatidylcholine, dipalmitoylphosphatidylcholine, dimyristoylphosphatidylcholine, dilauroylphosphatidylcholine, dioleylphophatidylcholine, hydrogenated egg phosphatidylcholine, soy phosphatidylcholine, hydrogenated soy phosphatidylcholine, and egg phosphatidylcholine.

18. A pH-sensitive liposome in accordance with claim 13 wherein said lipid is a mixture of egg phosphatidylcholine, dimyristoylphosphatidylcholine, dipalmitoylphosphatidylcholine and distearoylphosphotidylcholine.

19. A pH-sensitive liposome in accordance with claim 13 further comprising cholesterol.

20. A pH-sensitive liposome in accordance with claim 19 wherein said lipid is egg phosphatidylcholine.

21. A pH-sensitive liposome in accordance with claim 13 further comprising a bilayer stabilizing component.

22. A pH-sensitive liposome in accordance with claim 13 wherein said bilayer stabilizing component is a member selected from the group consisting of lipids, lipid derivatives, detergents, proteins, peptides, polyethylene glycol and N-(.omega.-N'-acetoxy-octa(14'amino-3',6'9',12'-tetraoxatetradecanoyl)) (ATTA).

23. A pH-sensitive liposome in accordance with claim 22 wherein said polyethylene glycol has a molecular weight ranging from about 200 to 10,000.

24. A pH-sensitive liposome in accordance with claim 22 wherein said ATTA has a molecular weight ranging from about 200 to 10,000.

25. A pH-sensitive liposome in accordance with claim 22 wherein said polyethylene glycol has a molecular weight ranging from about 2,000 to 6,000.

26. A pH-sensitive liposome in accordance with claim 22 wherein said ATTA has a molecular weight ranging from about 2,000 to 6,000.

27. A pH-sensitive liposome in accordance with claim 13 wherein said compound is present at a concentration ranging from about 1 weight percent to about 22 weight percent of said lipid.

28. A pH-sensitive liposome in accordance with claim 27 wherein said compound is present at a concentration ranging from about 2 percent to about 20 percent of lipid in a weight to weight ratio.

29. A pH-sensitive liposome in accordance with claim 27 wherein said compound is sent at a concentration on ranging from about 8 percent to about 10 percent of lipid.

30. A pH-sensitive liposome in accordance with claim 19 wherein said cholesterol is present at a concentration ranging from about 0.02 mole percent to about 50 mole percent.

31. A pH-sensitive liposome in accordance with claim 19 wherein said cholesterol is present at a concentration ranging from about 40 mole percent to about 45 mol percent.

32. A pH-sensitive liposome in accordance with claim 13 wherein said liposome becomes permeable, unstable or fusogenic at a rate which can be controlled by pH.

33. A pH-sensitive liposome in accordance with claim 13 wherein said liposome becomes destabilized at a rate which can be controlled by pH.

34. A pH-sensitive liposome in accordance with claim 13 wherein said liposome becomes fusogenic at a rate which can be varied over a pH range of about 3 to about 10.

35. A pH-sensitive liposome in accordance with claim 13 wherein said liposome becomes destabilized at a rate which can be controlled by varying Y.

36. A pH-sensitive liposome in accordance with claim 35 wherein Y is different in every other monomer n.

37. A pH-sensitive liposome in accordance with claim 35 wherein Y is different in every other monomer i.

38. A method for delivering a therapeutic compound to a target cell comprising administering to a host containing said target cell a pH-sensitive liposome of claim 13.

39. A method in accordance with claim 38 further comprising a bilayer stabilizing component, wherein said bilayer stabilizing component is a member selected from the group consisting of lipids, lipid derivatives, detergents, proteins, peptides, polyethylene glycol and ATTA.

40. A method in accordance with claim 38 wherein said liposome further comprises cholesterol.

41. A method in a accordance with claim 38 wherein said liposome is fusogenic over a pH range from 4 to 7.

42. A method in accordance with claim 38 wherein said liposome is administered intravenously.

43. A method in accordance with claim 38 wherein said liposome is administered parenterally.

44. A method in accordance with claim 38 wherein said liposome administered to said host is unilamellar.

45. A method in accordance with claim 44 wherein said unilamellar liposome has a mean diameter of 0.05 microns to 0.45 microns.

46. A method in accordance with claim 45 wherein said unilamellar liposome has a mean diameter of 0.05 microns to 0.2 microns.

* * * * *

UNITED STATES PATENT AND TRADEMARK OFFICE
CERTIFICATE OF CORRECTION

PATENT NO. : 6,986,902 B1  Page 1 of 1
APPLICATION NO. : 09/674191
DATED : January 17, 2006
INVENTOR(S) : Tao Chen et al.

It is certified that error appears in the above-identified patent and that said Letters Patent is hereby corrected as shown below:

Column 31
Line 1, "in with" should read as --in accordance with--

Column 32
Line 9, "3',6'9', 12'"" should read as --3',6',9',12'--
Line 33, "is sent at a concentration on ranging" should read as -- is present at a concentration ranging--
Line 40, "mol" should read as --mole--

Signed and Sealed this

Twenty-first Day of November, 2006

JON W. DUDAS
*Director of the United States Patent and Trademark Office*